(12) United States Patent
Mitchell

(10) Patent No.: US 10,806,770 B2
(45) Date of Patent: Oct. 20, 2020

(54) POWDER FORMULATION

(71) Applicant: GLAXOSMITHKLINE INTELLECTUAL PROPERTY DEVELOPMENT LIMITED, Brentford, Middlesex (GB)

(72) Inventor: James John Mitchell, Ware (GB)

(73) Assignee: MONASH UNIVERSITY, Victoria (AU)

(*) Notice: Subject to any disclaimer, the term of this patent is extended or adjusted under 35 U.S.C. 154(b) by 215 days.

(21) Appl. No.: 15/521,414

(22) PCT Filed: Oct. 29, 2015

(86) PCT No.: PCT/IB2015/058373
§ 371 (c)(1),
(2) Date: Apr. 24, 2017

(87) PCT Pub. No.: WO2016/067252
PCT Pub. Date: May 6, 2016

(65) Prior Publication Data
US 2019/0125824 A1 May 2, 2019

Related U.S. Application Data

(60) Provisional application No. 62/073,821, filed on Oct. 31, 2014, provisional application No. 62/189,252, filed on Jul. 7, 2015.

(51) Int. Cl.
*A61K 38/12* (2006.01)
*A61K 38/095* (2019.01)
*A61K 9/00* (2006.01)
*A61K 9/16* (2006.01)
*A61K 9/50* (2006.01)
*A61K 9/14* (2006.01)
*A61P 7/04* (2006.01)

(52) U.S. Cl.
CPC ............ *A61K 38/095* (2019.01); *A61K 9/008* (2013.01); *A61K 9/0075* (2013.01); *A61K 9/145* (2013.01); *A61K 9/1611* (2013.01); *A61K 9/1617* (2013.01); *A61K 9/1623* (2013.01); *A61K 9/5084* (2013.01); *A61P 7/04* (2018.01)

(58) Field of Classification Search
None
See application file for complete search history.

(56) References Cited

U.S. PATENT DOCUMENTS

| 4,402,942 | A | 9/1983 | Melin |
|---|---|---|---|
| 5,419,315 | A | 5/1995 | Rubsamen |
| 5,558,085 | A | 9/1996 | Rubsamen |
| 5,948,749 | A | 9/1999 | Igarashi et al. |
| 5,952,008 | A | 9/1999 | Backstrom et al. |
| 5,960,792 | A | 10/1999 | Lloyd et al. |
| 5,976,574 | A | 11/1999 | Gordon |
| 5,985,248 | A | 11/1999 | Gordon et al. |
| 6,001,336 | A | 12/1999 | Gordon |
| 6,004,574 | A | 12/1999 | Backstrom et al. |
| 6,012,450 | A | 1/2000 | Rubsamen |
| 6,077,543 | A | 6/2000 | Gordon et al. |
| 6,258,341 | B1 | 7/2001 | Foster et al. |
| 6,365,190 | B1 | 4/2002 | Gordon et al. |
| 6,447,806 | B1 | 9/2002 | Gassmann et al. |
| 6,453,758 | B1 | 9/2002 | Marple et al. |
| 6,509,006 | B1 | 1/2003 | Platz et al. |
| 6,543,301 | B2 | 4/2003 | Marple et al. |
| 6,565,885 | B1 | 5/2003 | Tarara et al. |
| 6,582,728 | B1 | 6/2003 | Platz et al. |
| 6,586,008 | B1 | 7/2003 | Batycky et al. |
| 6,595,368 | B2 | 7/2003 | Roberts et al. |
| 6,632,456 | B1 | 10/2003 | Bäckström et al. |
| 6,706,892 | B1 | 3/2004 | Ezrin et al. |
| 6,868,853 | B1 | 3/2005 | Nilsson et al. |
| 7,186,401 | B2 | 3/2007 | Keller et al. |
| 7,252,840 | B1 | 8/2007 | Batycky et al. |
| 7,448,379 | B2 | 11/2008 | Yamashita et al. |
| 7,694,357 | B2 | 4/2010 | Alvite |
| 7,735,485 | B2 | 6/2010 | Yamashita et al. |
| 8,211,405 | B2 | 7/2012 | Mueller-Walz et al. |
| 8,246,935 | B2 | 8/2012 | Mueller-Walz et al. |

(Continued)

FOREIGN PATENT DOCUMENTS

| AU | 702150 | 10/1996 |
|---|---|---|
| AU | 730059 | 11/1997 |

(Continued)

OTHER PUBLICATIONS

M. T. Newhouse, P. H. Hirst, S. P. Duddu, Y. H. Walter, T. E. Tarara, A. R. Clark, and J. G. Weers. Inhalation of a dry powder tobramycin pulmosphere formulation in healthy volunteers, Chest124:360-366 (2003). [PubMed].

P. H. Hirst, G. R. Pitcairn, J. G. Weers, T. E. Tarara, A. R. Clark, L. A. Dellamary, G. Hall, J. Shorr, and S. P. Newman. In vivo lung deposition of hollow porous particles from a pressurized metered dose inhaler. Pharm. Res.19:258-264 (2002). [PubMed].

S. P. Duddu, S. A. Sisk, Y. A. Walter, T. E. Tarara, K. E. Trimble, A. R. Clark, M. A. Eldon, R. C. Elton, M. Pickford, P. H. Hirst, S. P. Newman, and J. G. Weers. Improved lung delivery from a passive dry powder inhaler using an engineered pulmoshpere powder. Pherm. Res.9:689-695 (2002). [PubMed].

(Continued)

*Primary Examiner* — Satyanarayana R Gudibande
(74) *Attorney, Agent, or Firm* — Honigman LLP; Kelly T. Murphy

(57) ABSTRACT

Methods of reducing chemical degradant formation, such as those resulting from dimer formation in disulfide bridge-closed ring-bearing polypeptides, such as oxytocin, in a solid-state; to heat stable pharmaceutical compositions having improved physio- or chemical stability, to inhalers and dosage forms of such compositions, to methods of production of and treatment of diseases and or conditions, such as post partum hemhorrage, with such compositions.

29 Claims, 10 Drawing Sheets

Specification includes a Sequence Listing.

(56) References Cited

U.S. PATENT DOCUMENTS

| | | | |
|---|---|---|---|
| 8,268,358 B2 | 9/2012 | Batycky et al. | |
| 8,414,867 B2 | 4/2013 | Mueller-Walz et al. | |
| 8,679,540 B2 | 3/2014 | Bonnet-Gonnet et al. | |
| 8,758,824 B2 | 6/2014 | Lipp et al. | |
| 8,992,983 B2 | 3/2015 | Lipp et al. | |
| 9,433,576 B2 | 9/2016 | Lipp et al. | |
| 9,925,144 B2 * | 3/2018 | Fabio | A61K 38/095 |
| 2003/0181387 A1 | 9/2003 | Vickery et al. | |
| 2003/0232020 A1 | 12/2003 | York et al. | |
| 2003/0235536 A1 | 12/2003 | Blumberg et al. | |
| 2003/0235537 A1 | 12/2003 | Bartus et al. | |
| 2004/0096403 A1 | 5/2004 | Steiner et al. | |
| 2004/0171550 A1 | 9/2004 | Backstrom et al. | |
| 2004/0184995 A1 | 9/2004 | Katsuma et al. | |
| 2005/0014677 A1 | 1/2005 | Lizio et al. | |
| 2005/0048116 A1 | 3/2005 | Straub et al. | |
| 2005/0191246 A1 | 9/2005 | Bechtold-Peters et al. | |
| 2008/0026070 A1 | 1/2008 | Bonnet-Gonnet | |
| 2008/0089849 A1 | 4/2008 | Schultz-Fademrecht et al. | |
| 2008/0102128 A1 | 5/2008 | Constancis et al. | |
| 2009/0142407 A1 | 6/2009 | Lizio et al. | |
| 2009/0226530 A1 | 9/2009 | Lassner et al. | |
| 2010/0092453 A1 | 4/2010 | Healy et al. | |
| 2010/0144625 A1 | 6/2010 | Mueller-Walz | |
| 2010/0197565 A1 | 8/2010 | Smutney et al. | |
| 2010/0310660 A1 | 12/2010 | Tsai et al. | |
| 2011/0208168 A1 | 8/2011 | Eliaz et al. | |
| 2013/0014758 A1 | 1/2013 | Mueller-Walz et al. | |
| 2013/0071440 A1 | 3/2013 | Batycky et al. | |
| 2013/0149345 A1 | 6/2013 | Lipp et al. | |
| 2013/0164338 A1 | 6/2013 | Lipp et al. | |
| 2014/0079782 A1 | 3/2014 | York et al. | |
| 2014/0212504 A1 | 7/2014 | Weers et al. | |
| 2014/0242116 A1 | 8/2014 | Poe et al. | |
| 2015/0004233 A1 | 1/2015 | Lipp et al. | |
| 2015/0202227 A1 | 7/2015 | Lipp et al. | |
| 2017/0224762 A1 | 8/2017 | McIntosh et al. | |

FOREIGN PATENT DOCUMENTS

| | | |
|---|---|---|
| AU | 756852 | 6/2000 |
| AU | 764738 | 3/2001 |
| AU | 2002222115 B2 | 6/2002 |
| AU | 2004288644 B2 | 5/2005 |
| AU | 2009204863 B2 | 7/2009 |
| AU | 20112711097 B2 | 12/2011 |
| CA | 2382651 | 3/2001 |
| CN | 011317821 | 12/2008 |
| CN | 102228678 A | 11/2011 |
| CN | 103110611 A | 5/2013 |
| EP | 0360340 A1 | 3/1990 |
| EP | 0681491 A1 | 8/1994 |
| EP | 0706383 B1 | 4/1996 |
| EP | 0788388 A2 | 5/1996 |
| EP | 0817655 B1 | 10/1999 |
| EP | 0592540 B1 | 1/2000 |
| EP | 0681491 B1 | 12/2000 |
| EP | 0788388 B1 | 4/2002 |
| EP | 0799030 B1 | 7/2002 |
| EP | 1131059 B1 | 3/2003 |
| EP | 1019022 B1 | 4/2003 |
| EP | 1019023 B1 | 5/2003 |
| EP | 0941067 B1 | 7/2003 |
| EP | 0806938 B1 | 12/2003 |
| EP | 0825885 B1 | 3/2004 |
| EP | 0820277 B1 | 1/2005 |
| EP | 1210068 B1 | 3/2006 |
| EP | 1637128 A2 | 3/2006 |
| EP | 1402913 B1 | 8/2006 |
| EP | 1232745 B1 | 3/2007 |
| EP | 1359902 B1 | 8/2007 |
| EP | 1296651 B1 | 11/2007 |
| EP | 1862164 A2 | 12/2007 |
| EP | 1283036 B1 | 1/2008 |
| EP | 1337241 B1 | 1/2008 |
| EP | 0846009 B1 | 3/2008 |
| EP | 1658047 B1 | 3/2008 |
| EP | 1913939 A1 | 4/2008 |
| EP | 1337239 B1 | 10/2009 |
| EP | 1479300 B1 | 10/2009 |
| EP | 2168571 A2 | 3/2010 |
| EP | 2326341 A1 | 3/2010 |
| EP | 2266548 A2 | 12/2010 |
| EP | 2272508 A2 | 1/2011 |
| EP | 2283817 A1 | 2/2011 |
| EP | 2283818 A1 | 2/2011 |
| EP | 2292212 A2 | 3/2011 |
| EP | 2298279 A2 | 3/2011 |
| EP | 2311434 A1 | 4/2011 |
| EP | 1829533 B1 | 6/2011 |
| EP | 2298285 A3 | 7/2011 |
| EP | 1666023 B1 | 10/2011 |
| EP | 1663155 B1 | 11/2011 |
| EP | 2315580 B1 | 12/2011 |
| EP | 2326341 B1 | 7/2012 |
| EP | 2526990 A2 | 11/2012 |
| EP | 2448571 B1 | 6/2013 |
| EP | 1920763 B1 | 4/2014 |
| EP | 2174653 B1 | 5/2014 |
| EP | 1337240 B2 | 9/2014 |
| GB | 2351155 A | 12/2000 |
| GB | 2371001 A | 7/2002 |
| GB | 2371247 A | 7/2002 |
| IN | 00953MUM2006 | 6/2006 |
| JP | 2007077048 A | 3/2007 |
| WO | 1991016038 A1 | 10/1991 |
| WO | 1991016882 A1 | 11/1991 |
| WO | 1992018105 A1 | 10/1992 |
| WO | 1993025198 A1 | 12/1993 |
| WO | 1994016756 A1 | 8/1994 |
| WO | 1995000128 A1 | 1/1995 |
| WO | 1996013290 A1 | 5/1996 |
| WO | 1996019197 A1 | 6/1996 |
| WO | 1996019207 A1 | 6/1996 |
| WO | 1996030068 A1 | 10/1996 |
| WO | 1996032096 A1 | 10/1996 |
| WO | 1996032149 A1 | 10/1996 |
| WO | 1996032152 A1 | 10/1996 |
| WO | 1996036314 A2 | 11/1996 |
| WO | 1997003649 A1 | 2/1997 |
| WO | 1997035562 A1 | 10/1997 |
| WO | 1997036574 | 10/1997 |
| WO | 1997040819 A1 | 11/1997 |
| WO | 1997041833 A1 | 11/1997 |
| WO | 1997044013 A1 | 11/1997 |
| WO | 1998007410 A1 | 2/1998 |
| WO | 1998/16205 A2 | 4/1998 |
| WO | 199816205 A2 | 4/1998 |
| WO | 19980016205 | 4/1998 |
| WO | 1998/29098 A1 | 7/1998 |
| WO | 1998/29141 A1 | 7/1998 |
| WO | 1998029096 A1 | 7/1998 |
| WO | 1998029097 A1 | 7/1998 |
| WO | 1998029140 A1 | 7/1998 |
| WO | 19980029098 | 7/1998 |
| WO | 19980029141 | 7/1998 |
| WO | 1998041193 A1 | 9/1998 |
| WO | 1998050015 A1 | 11/1998 |
| WO | 1999010011 | 3/1999 |
| WO | 1999016419 A1 | 4/1999 |
| WO | 1999016420 A1 | 4/1999 |
| WO | 1999016421 A1 | 4/1999 |
| WO | 1999016422 A1 | 4/1999 |
| WO | 1999024019 A1 | 5/1999 |
| WO | 1999032083 A1 | 7/1999 |
| WO | 1999038527 A1 | 8/1999 |
| WO | 1999047196 A1 | 9/1999 |
| WO | 2000010541 A1 | 3/2000 |
| WO | 2000015262 A1 | 3/2000 |
| WO | 2000/28979 A1 | 5/2000 |
| WO | 2000028979 | 5/2000 |
| WO | 2000033811 A2 | 6/2000 |
| WO | 2001003821 A1 | 1/2001 |
| WO | 2001/13891 A2 | 3/2001 |

(56) References Cited

FOREIGN PATENT DOCUMENTS

| | | |
|---|---|---|
| WO | 2001013891 A2 | 3/2001 |
| WO | 2001013892 A2 | 3/2001 |
| WO | 2001013893 A2 | 3/2001 |
| WO | 2001017568 A2 | 3/2001 |
| WO | 2001017614 A2 | 3/2001 |
| WO | 2001051030 A1 | 7/2001 |
| WO | 2001058425 A2 | 8/2001 |
| WO | 2001060341 A1 | 8/2001 |
| WO | 2001078696 A2 | 10/2001 |
| WO | 2001082906 A1 | 11/2001 |
| WO | 2001085137 A2 | 11/2001 |
| WO | 2001093837 A2 | 12/2001 |
| WO | 2002000197 A1 | 1/2002 |
| WO | 2002011803 A1 | 2/2002 |
| WO | 2002015876 A2 | 2/2002 |
| WO | 2002018000 A1 | 3/2002 |
| WO | 2002045690 A1 | 6/2002 |
| WO | 2002053190 A2 | 7/2002 |
| WO | 2002055101 A2 | 7/2002 |
| WO | 2002062317 A2 | 8/2002 |
| WO | 2002066078 A2 | 8/2002 |
| WO | 2002067902 B2 | 9/2002 |
| WO | 2002078675 A2 | 10/2002 |
| WO | 2002080884 A2 | 10/2002 |
| WO | 2002102445 A1 | 12/2002 |
| WO | 2003007867 A2 | 1/2003 |
| WO | 2003015750 A1 | 2/2003 |
| WO | 2003024396 A2 | 3/2003 |
| WO | 2003/35034 A2 | 5/2003 |
| WO | 2003035034 A2 | 5/2003 |
| WO | 2003035051 A2 | 5/2003 |
| WO | 2003037303 A1 | 5/2003 |
| WO | 2003043585 A2 | 5/2003 |
| WO | 2003043586 A2 | 5/2003 |
| WO | 2003059324 A1 | 7/2003 |
| WO | 2003072080 A1 | 9/2003 |
| WO | 2003077834 A2 | 9/2003 |
| WO | 2003079991 A2 | 10/2003 |
| WO | 2003079993 A2 | 10/2003 |
| WO | 2003086358 A1 | 10/2003 |
| WO | 2003086443 A1 | 10/2003 |
| WO | 2004004798 A2 | 1/2004 |
| WO | 2004030659 A1 | 4/2004 |
| WO | 2004054555 A1 | 7/2004 |
| WO | 2004058156 A2 | 7/2004 |
| WO | 2004062560 A2 | 7/2004 |
| WO | 2004082750 A1 | 9/2004 |
| WO | 2005020953 A1 | 3/2005 |
| WO | 2005035088 A2 | 4/2005 |
| WO | 2005/46636 A1 | 5/2005 |
| WO | 2005044186 A2 | 5/2005 |
| WO | 2005046636 A1 | 5/2005 |
| WO | 2005069100 A2 | 7/2005 |
| WO | 2005079755 A2 | 9/2005 |
| WO | 2005084638 A2 | 9/2005 |
| WO | 2005/92289 A1 | 10/2005 |
| WO | 2005/96845 A1 | 10/2005 |
| WO | 2005092289 A1 | 10/2005 |
| WO | 2005096845 A1 | 10/2005 |
| WO | 2005077338 A1 | 11/2005 |
| WO | 2005/112892 A1 | 12/2005 |
| WO | 2005112892 | 12/2005 |
| WO | 2005113007 A2 | 12/2005 |
| WO | 2005055976 A2 | 2/2006 |
| WO | 2005044187 A2 | 3/2006 |
| WO | 2006033604 A1 | 3/2006 |
| WO | 2006055950 A1 | 5/2006 |
| WO | 2006008517 A2 | 11/2006 |
| WO | 2006121791 A1 | 11/2006 |
| WO | 2006125153 A2 | 11/2006 |
| WO | 2006076265 A2 | 12/2006 |
| WO | 2007014391 A2 | 2/2007 |
| WO | 2007045689 A2 | 4/2007 |
| WO | 2007068443 A1 | 6/2007 |
| WO | 2007042822 A2 | 7/2007 |
| WO | 2007095288 A2 | 8/2007 |
| WO | 2007/141344 A2 | 12/2007 |
| WO | 2007141344 A2 | 12/2007 |
| WO | 2008013955 A2 | 1/2008 |
| WO | 2007098500 A2 | 2/2008 |
| WO | 2008/058691 A2 | 5/2008 |
| WO | 2008025425 A1 | 5/2008 |
| WO | 2008051363 A2 | 5/2008 |
| WO | 2008058691 A2 | 5/2008 |
| WO | 2008062429 A2 | 5/2008 |
| WO | 2008000780 A2 | 6/2008 |
| WO | 2007120644 A2 | 11/2008 |
| WO | 2008145730 A1 | 12/2008 |
| WO | 2008145732 A1 | 12/2008 |
| WO | 2009026434 A1 | 2/2009 |
| WO | 2009033701 A1 | 3/2009 |
| WO | 2009033724 A1 | 3/2009 |
| WO | 2009033744 A1 | 3/2009 |
| WO | 2009/043458 A2 | 4/2009 |
| WO | 2009040020 A1 | 4/2009 |
| WO | 2009043439 A2 | 4/2009 |
| WO | 2009043448 A2 | 4/2009 |
| WO | 2009043457 A2 | 4/2009 |
| WO | 2009043458 A2 | 4/2009 |
| WO | 2009043466 A2 | 4/2009 |
| WO | 2009043527 A2 | 4/2009 |
| WO | 2009046440 A1 | 4/2009 |
| WO | 2009046844 A1 | 4/2009 |
| WO | 2009046852 A1 | 4/2009 |
| WO | 2009046861 A1 | 4/2009 |
| WO | 2009033735 A2 | 5/2009 |
| WO | 2009033717 A2 | 6/2009 |
| WO | 2009050217 A2 | 6/2009 |
| WO | 2009039990 A2 | 7/2009 |
| WO | 2009090189 A1 | 7/2009 |
| WO | 2009033795 A2 | 8/2009 |
| WO | 2009095681 A1 | 8/2009 |
| WO | 2009046865 A2 | 9/2009 |
| WO | 2009043505 A2 | 10/2009 |
| WO | 2009102467 A2 | 10/2009 |
| WO | 2009143011 A1 | 11/2009 |
| WO | 2009033707 A2 | 12/2009 |
| WO | 2010/030180 A2 | 3/2010 |
| WO | 2010/033220 A2 | 3/2010 |
| WO | 2010030180 A2 | 3/2010 |
| WO | 2010033220 A2 | 3/2010 |
| WO | 2009043450 A2 | 4/2010 |
| WO | 2010072621 A2 | 7/2010 |
| WO | 2010111640 A2 | 9/2010 |
| WO | 2010111644 A1 | 9/2010 |
| WO | 2010111650 A2 | 9/2010 |
| WO | 2010111680 A2 | 9/2010 |
| WO | 2010111641 A2 | 11/2010 |
| WO | 2010130982 A2 | 11/2010 |
| WO | 2010132827 A1 | 11/2010 |
| WO | 2011035330 A2 | 3/2011 |
| WO | 2011048379 A2 | 4/2011 |
| WO | 2011057235 A2 | 5/2011 |
| WO | 2010124198 A2 | 8/2011 |
| WO | 2011118960 A2 | 9/2011 |
| WO | 2011120779 A1 | 10/2011 |
| WO | 2010102148 A2 | 12/2011 |
| WO | 2010163272 A1 | 12/2011 |
| WO | 2011163272 A1 | 12/2011 |
| WO | 201230664 A1 | 3/2012 |
| WO | 2012024770 A1 | 3/2012 |
| WO | 2012028745 A1 | 3/2012 |
| WO | 2012030645 A1 | 3/2012 |
| WO | 2012030647 A1 | 3/2012 |
| WO | 2012030664 A1 | 3/2012 |
| WO | 201250945 A1 | 4/2012 |
| WO | 2012044736 A1 | 4/2012 |
| WO | 2012050945 A1 | 4/2012 |
| WO | 2012012498 A2 | 6/2012 |
| WO | 2012106575 A1 | 8/2012 |
| WO | 2013016754 A1 | 2/2013 |
| WO | 2013030645 A1 | 3/2013 |
| WO | 2013030647 A1 | 3/2013 |
| WO | 2013030664 A2 | 3/2013 |

(56) References Cited

FOREIGN PATENT DOCUMENTS

| WO | 2013052844 | A1 | 4/2013 |
|---|---|---|---|
| WO | 2013079605 | A2 | 6/2013 |
| WO | 2013113767 | A1 | 8/2013 |
| WO | 2013128283 | A2 | 9/2013 |
| WO | 2013128283 | A2 | 9/2013 |
| WO | 2013130767 | A1 | 9/2013 |
| WO | 2013130767 | A1 | 9/2013 |
| WO | 2012051426 | A2 | 10/2013 |
| WO | 2014078258 | | 5/2014 |
| WO | 2015010092 | A1 | 1/2015 |
| WO | 2016067252 | A1 | 5/2016 |

OTHER PUBLICATIONS

T. E. Tarara, M. S. Hartman, H. Gill, A. A. Kennedy, and J. G. Weers. Characterization of suspension-based metered dose inhaler formulations composed of spray-dried budesonide microcrystals dispersed in HFA-134a. Pharm. Res.21:1607-1614 (2004). [PubMed].
J.D. Andya, Y.-F. Maa, H. R. Costantino, P.-A. Nguyen, N. Dasovich, T. D. Sweeney, C. C. Hsu, and S. J. Shire. The effect of formulation excipients on protein stability and aerosol performance of spray-dried powders of a recombinant humanized anti-IgE monoclonal antibody. Pharm. Res.16:350-358 (1999). [PubMed].
Bot, D. J. Smith, S. Bot, L. Dellamary, T. E. Tarara, S. Harders, W. Phillips, J. G. Weers, and C. M. Woods. Receptor-mediated targeting of spray-dried lipid particles coformulated with immunoglobulin and loaded with a prototype vaccine. Pharm. Res.18:971-979 (2001). [PubMed].
J. Weers, T. Tarara, R. Malcolmson, and D. Leung. Embedded crystals in low density particles: formulation, manufacture, and properties. Respir. Drug Deliv. Proc.X:297-306 (2006).
Avanti et al., A New Stragegy to Stablizie Oxytocin in Aqueous Solutions: I. The Effects of Divalent Metal Ions and Citrate Buffer. AAPS Journal vol. 13, No. 2, Jun. 2011.
Avantia et al.,A New Strategy to Stablize Oxytocin in Aqueous Solutions: II. Suppression of Cysteine-Mediated Intermolecular Reactions by a Combination of Divalent Metal Ions and Citrate. Mol. Pharmaceutics 9, 544-562, 2012.
Chan, Hak-Kim et al., Spray Dried Powders and Powder Blends of Recombinant Human Deoxyribonuclease (rhDNase) for Aerosol Delivery1. Pharmaceutical Research[0724-8741],Cyr:1997vol. 14:4 p. 431-437.
Oxytocin. European Pharmacopoeia 7.0, pp. 2653-2654 (2011).
Nano Spray Dryer B90 Literature Review andApplications. www.buchi.com, Information Bulletin No. 63/2011.
Shur et al., Cospray-Dried Unfractionated Heparin with L-Leucine as a Dry Powder Inhaler Mucolytic for Cystic Fibrosis Therapy. Journal of Pharmaceutical Sciences, vol. 97, No. 11, 4857-4868, 2008.
Sou et al, The effect of amino acid excipients on morphology and solid-state properties of multi-component spray-dried formulations for pulmonary delivery of biomacromolecules. European journal of pharmaceutics and biopharmeceutics[0939-6411]:2013vol. 83iss:2p. 234.
Oxytetracycline Hydrochloride and Polymyxin B Sulfate Topical Powder. The United States Pharmacopeial Convention. Official Monographs, USP 35, 4192-4193.
Reinhard Vehring. Pharmaceutical Particle Engineering via Spray Drying. Pharm Res. May 2008; 25(5): 999-1022.
You et al, Physical characteristics and aerosolization performance of inulin dry powders for inhalation prepared by a spray drying method. JPP 2007, 59: 927-934.
Anonymous, Oxytocin. European Pharmacopoeia 7.0, p. 2653 (2011).
Callahan, Oxytocin. U.S. Pharmacopeia retrieved Mar. 17, 2017 online at: http://www.pharmacopeia.cn/v29240/usp29nf24s0_m60145.html. 2 pages.
World Health Organization, Oxytocin: Adopted Text for the International Pharmacopoeia. Final text for addition to the International Pharmacopoeia. Working document QAS/07.241/FINAL, Jun. 2010, 7 pages.
Zaidi, Aerosols, Nasal Sprays, Metered-Dose Inhalers, and Dry Powder Inhalers. U.S. Pharmacopeia, retrieved Mar. 17, 2017 online http://www.pharmacopeia.cn/v29240/usp29nf24s0_c601_viewall.html, 31 pages.
Chan, "Spray Dried Powders and Powder Blends of Recombinant Human Deoxyribonuclease (rhDNase) for Aerosol Delivery." Pharm. Res.; 1997; vol. 14(4) pp. 431-437.
Gent, "Changes in intra-uterine pressure due to intranasal administration of oxytocin (Partocon)" Acta Obsterica et Gynocolica Scandanavica, 1967) vol. 46, No. 3, pp. 340-53 (ISSN: 0001-6349. L-ISSN: 001-6349.
Green, "Uterine Rupture following intranasal Oxytocin" The New Zealand Medical Journal, (Feb. 1965) vol. 64, pp. 79-80. ISSN: 0028-8446. L-ISSN: 0028-8446.
Niven, "Delivery of Biotherapeutics by Inhalation Aerosols" Pharm Technol (17, July Suppl., 72-82, 1993). ISSN: 0147-8087.
"Recherches dans le post-partum. Role et avantages de l'ocytocine synthetique en vaporisateur nasal" Un. Med. Can. (1962) vol. 91, No. 11, pp. 684-690.
Tutschek, "Silent Uterine Rupture" Ultrasound in Obstetrics and Gynacology, Aug. 2005) vol. 26, No. 2, pp. 199-200 (ISSN: 0960-7692).
"Aerosols, Nasal Sprays, Metered-Dose Inhalers, and Dry Powder Inhalers" U.S. Phamrmacopeia, pp. 1-37.
"Uniformity of Dosage Units." U.S. Pharmacopeia, pp. 1-6.
Pitocin_oxyticin Injection USP Synthetic_US Label, pp. 1-7.

\* cited by examiner

SEQUENCE LISTING

<160> NUMBER OF SEQ ID NOS: 1

<210> SEQ ID NO 1
<211> LENGTH: 9
<212> TYPE: PRT
<213> ORGANISM: Homo Sapien

<400> SEQUENCE: 1

Cys Tyr Ile Gln Asn Cys Pro Leu Gly
1               5

POWDER FORMULATION

CROSS REFERENCE TO RELATED PATENTS AND PATENT APPLICATIONS

This application is a 371 of International Application No PCT/IB2015/058373, filed Oct. 29, 2015, which claims the benefit of U.S. Provisional Patent Application No. 62/073,821 filed on Oct. 31, 2014 and U.S. Provisional Application No. 62/189,252 filed on Jul. 7, 2015, both of which are hereby incorporated by reference in their entirety.

FIELD OF THE INVENTION

The present invention relates generally to the methods of reducing chemical degradant formation, such as those resulting from dimer formation, associated with disulfide bridge-closed ring-bearing polypeptides, such as oxytocin, in a solid-state. It also relates to pharmaceutical compositions having improved physio- or chemical stability, to inhalers and dosage forms of such compositions, as well as to methods of production of and treatment of diseases and or conditions with such compositions.

BACKGROUND

Oxytocin is a nine amino acid polypeptide. Its systematic name is cysteine-tyrosine-isoleucine-glutamine-asparagine-cysteine-proline-leucine-glycine-amide (cys-tyr-ile-gln-asn-cys-pro-leu-gly-$NH_2$), and it chemical name (IUPAC) is 1-({(4R,7S,10S,13S,16S,19R)-19-amino-7-(2-amino-2-oxoethyl)-10-(3-amino-3-oxopropyl)-16-(4-hydroxybenzoyl)-13-[(1S)-1-methylpropyl]-6,9,12,15,18-pentaoxo-1,2-dithia-5,8,11,14,17-pentaazacycloicosan-4-yl}carbonyl)-L-prolyl-L- leucylglycinamide. Oxytocin has a molecular mass of 1007 daltons. One international unit (IU) of oxytocin is the equivalent of about 2 micrograms (μg or mcg) of pure peptide.

Oxytocin plays a number of very important roles in mammalian physiology, including inducing uterine contraction prior to and during childbirth, as well as assistance in blood clotting after childbirth. Thus, medical indications for oxytocin include labor inducement, improvement in the regularity of contractions, as well as the prevention of post partum hemorrhage.

While oxytocin is readily available in the developed world in brand name and generic forms, these have been primarily in intravenous (IV) and intramuscular (IM) injectable dosages and, to a much lesser extent, in intranasal form. Global availability of oxytocin in an injectable form is significantly hampered by the fact that oxytocin is heat labile, and requires refrigeration to avoid chemical degradation. This heat sensitivity makes the viability of the product in areas of the world lacking consistently available electricity very limited. Further, as an injectable, the dosage form requires sterile needles and a trained healthcare staff to administer the product appropriately, which may be difficult to secure in resource-poor settings.

These limitations of current therapies have very serious implications. Maternal death during childbirth in the developing world from complication addressable by oxytocin therapy number in the hundreds of thousand each year. Access to oxytocin in the developing world has the potential to prevent tens of millions of post partum hemorrhage cases, and many million deaths over the course of a decade.

The challenges faced by existing aqueous forms have led a number of groups to attempt to formulate oxytocin as a heat stable dry powder. Various inhaled oxytocin formulations are disclosed in the patent and scientific literature.

In an effort to address this need, WO130016754 describes a heat stable formulation of inhalable peptides, such as oxytocin, where the oxytocin is presented as a respirable dry powder composite, produced via spray drying from a solution, with excipients, such as carbohydrates, (e.g., trehalose) and amino acids (e.g., L-leucine). In comparison with the injectable form, such an inhalable dry powder form of oxytocin was reported to be heat stable and more suitable for therapeutic use in hot climates, which are resource poor. Moreover, this inhalable form could be delivered from a simple unit dose inhaler, thus capable of being administered without sterile needles or the assistance of specially trained medical personnel, thus allowing for self-administration or administration by a lay assistant.

Investigation of such dry powder formulations, although very promising, could be improved upon, for example, by improving chemical stability of such formulations, such as by, for example, reducing peptide-related impurities and other degradants which form on storage as a result of physiochemical instability.

Among the known and potential impurities in oxytocin materials are carbimido oxytocin, acetyloxytocin, and both an α-dimer, and a β-dimer of oxytocin. (See, for example, the *World Health Organization, Oxytocin: Adopted Text For The International Pharmacopoeia* (June 2010)).

As described in the International Pharmacopeia, "carbimido oxytocin" has the chemical name, N-(L-cysteinyl-L-tyrosyl-L-isoleucyl-L-glutaminyl-L-asparaginyl-L-cysteinyl-L-prolyl-L-leucylglycyl)urea cyclic-(1→6)-disulfide, and the following structure:

$$\text{H-Cys-Tyr-Ile-Gln-Asn-Cys-Pro-Leu-Gly-NH} \overset{O}{-}\text{NH}_2$$

"Acetyloxytocin" has the chemical name, acetyl-L-cysteinyl-L-tyrosyl-L-isoleucyl-L-glutaminyl-L-asparaginyl-L-cysteinyl-L-prolyl-L-leucylglycinamide cyclic-(1→6)-disulfide, and the following structure:

$$H_3C\overset{O}{-}\text{Cys-Tyr-Ile-Gln-Asn-Cys-Pro-Leu-Gly-NH}_2$$

"α-oxytocin dimer" has the chemical name, L-cysteinyl-L-tyrosyl-L-isoleucyl-L-glutaminyl-L-asparaginyl-L-cysteinyl-L-prolyl-L-leucylglycinamide dimer (1→1':6→6')-bisdisulfide, and the following structure:

$$\begin{array}{c}\text{H-Cys-Tyr-Ile-Gln-Asn-Cys-Pro-Leu-Gly-NH}_2\\|\qquad\qquad\qquad|\\\text{H-Cys-Tyr-Ile-Gln-Asn-Cys-Pro-Leu-Gly-NH}_2\end{array}$$

and

β-oxytocin dimer has the following chemical name, L-cysteinyl-L-tyrosyl-L-isoleucyl-L-glutaminyl-L-asparaginyl-L-cysteinyl-L-prolyl-L-leucylglycinamide dimer (1→6':1'→6)-bisdisulfide, and the following structure:

H-Cys-Tyr-Ile-Gln-Asn-Cys-Pro-Leu-Gly-NH$_2$
H-Cys-Tyr-Ile-Gln-Asn-Cys-Pro-Leu-Gly-NH$_2$

Under the European Pharmacopeia, in order to meet European Pharmacopeia standards, the limit on any impurity is 1.5%, and the total limit is a maximum of 5% impurities (see, *European Pharmacopeia* 7.0, *Oxytocin,* 01/2008:0780 *corrected* 6.0). As stated in the US Pharmacopeia for Oxytocin, the sum of the responses of impurities in the chromatogram of the Assay preparation obtained in the Assay is not more than 5% of the area of the oxytocin peak (see, *USP* 35 *Official Monograph, Oxytocin, p.* 4192-1493 (August 2012)).

The following invention represents a further improvement of such powder formulations.

SUMMARY OF THE INVENTION

In the development of a heat stable, dry powder oxytocin product, applicant recognized that formation of the degradants, such as α-oxytocin dimer and β-oxytocin dimer impurities resulted from the cleavage of the disulfide bridge of one oxytocin molecule, and the reformation of disulfide bridges with the free thiol groups present on an adjacent, similarly "open", oxytocin molecule.

Applicant believes, without being bound to any particular theory, that providing a positively charged ($^{+2}$) material in proximity to the anionic portions of the amino acids present in the ring structure of oxytocin would maintain the individual thiol portions the disulfide bridge in the ring of a single oxytocin molecule sufficiently close that, in the event that the disulfide bridge did break, the thiol groups would be held in proximity to each other for a sufficient period of time so as to allow for re-formation of the disulfide bridge within the single oxytocin molecule, rather than an adjacent free thiol of another oxytocin molecule, and thus reduce the formation of the α-oxytocin dimer and β-oxytocin dimer impurities.

Based on this rationale, applicant has designed a method for reducing dimer impurity formation in solid state, therapeutically active, disulfide bridge-closed ring-bearing polypeptides, such as oxytocin, vasopressin, etc., by inclusion of a molar equivalent amount or greater of a divalent cationic material.

Thus, in a first aspect, the present invention provides a method for increasing physiochemical stability of disulfide bridge-dosed ring-bearing polypeptides, such as oxytocin, in a solid state form, such as in a dry powder, comprising:

providing in a solid-phase composite particle, a molar equivalent amount or greater of divalent cation to each molar amount of disulfide bridge-closed ring-bearing polypeptide, wherein the particle comprises said ring-bearing polypeptide, said molar equivalent or greater amount of divalent cationic material, one or more carbohydrates and one or more hydrophobic amino acids.

In this context, "disulfide bridge-closed ring-bearing polypeptide" means a therapeutically active polypeptide possessing a ring structure which is closed by a disulfide bridge. Such disulfide bridge closed rings can open upon cleavage of the disulfide bridge, and the open ring form a chain. The disulfide bridge may re-form, thus causing the chain to once more assume its original ring structure. The ring itself may consist of any number of amino acids which is sufficiently long to form such a ring which may be closed by the disulfide bridge, and yet not so long so that the divalent cationic material no longer interacts with the anionic regions of the amino acid components of the ring to hold the thiol subcomponents which make up the disulfide bond in proximity, thus permitting the disulfide bond to re-form if it is broken. In one aspect, the present approach is directed to ring bearing polypeptides which are nonapeptides, with six of nine or the amino acids forming a disulfide bridge-closed ring, such as vasopressin or oxytocin. In a preferred aspect, the ring bearing polypeptide is oxytocin. Oxytocin, in the form of oxytocin acetate is used in the present application.

Dimer impurity content may be measured, for example, by measuring the amount of α-oxytocin dimer and/or β-oxytocin dimer in given disulfide bridge-closed ring-bearing polypeptide dry powder formulation which includes a divalent cationic material, and comparing this to a similar dry powder formulation lacking such divalent cation. Such testing, for example may be carried out as in any suitable manner, such as by use of Reverse Phase High Performance Liquid Chromatography. For oxytocin, such processes may be found in, for example, in the *European Pharmacopeia* 7.0, *Oxytocin,* 01/2008:0780 *corrected* 6.0; or US Pharmacopeia for Oxytocin, 35 *Official Monograph, Oxytocin,* p. 4192-1493 (August 2012).

In certain oxytocin-containing formulations of the present invention, the % of α-oxytocin dimer, by peak area response, is 1.75% a/a (area/area) or less of the total peptide content 60 days or more post dose production, as determined by HPLC (under conditions discussed below); in other embodiments, 1.5% a/a or less w/w of the total peptide content 60 days or more post dose production; or 1.25% a/a or less w/w of the total peptide content 60 days or more post dose production; or 1.0% a/a or less w/w of the total peptide content 60 days or more post dose production; or 0.75% a/a or less a/a of the total peptide content 60 days or more post dose production, such as 0.6% a/a or less w/w of the total peptide content 60 days or more post dose production.

In further embodiments of the oxytocin containing formulations of the present invention, the % of β-oxytocin dimer, by peak area response, is 1.75% a/a or less of the total peptide content 60 days or more post dose production, as determined by HPLC; in other embodiments, 1.5% a/a or less of the total peptide content 60 days or more post dose production; or 1.25% or less a/a of the total peptide content 60 days or more post dose production; or 1.0% a/a or less of the total peptide content 60 days or more post dose production; or 0.75% a/a or less of the total peptide content 60 days or more post dose production, such as 0.6% a/a or less of the total peptide content 60 days or more post dose production.

Thus, in a further aspect of the invention, we provide a pharmaceutical composition comprising a plurality of dry-powder composite particles, each composite particle comprising:

(i) an amount physiologically active disulfide bridge-closed ring-bearing polypeptide;
(ii) a molar equivalent amount or greater, to the amount of polypeptide, of divalent cationic material;
(iii) one or more carbohydrate; and
(iv) one or more amino acid.

In this further aspect of this aspect invention, the composite particles have an mean aerodynamic particle size less than 10 μm (MMAD), such as from about 5 μm to 0.5 μm, such as about 3 μm to about 0.5 μm. For a systemically therapeutically effective disulfide bridge-closed ring-bearing polypeptide, such particles are appropriately sized to be suitable for delivery to the alveolar region of the lung.

In certain embodiments of this aspect of the invention, the disulfide bridge-closed ring-bearing polypeptide comprises oxytocin (e.g. oxytocin acetate). The amount of oxytocin in the composite particles is 20% or less, for example, 15% of less, or about 10% or less of the mass of the plurality of composite particles. In various embodiments, the percentage w/w of the composite particle comprising oxytocin is, independently 20% or less, 19% or less, 18% or less, 17% or less, 16% or less, 15% or less, 14% or less, 13% or less, 12% or less, 11% or less, 10% or less, 9% or less, 8% or less, 7% or less, 6% or less, 5.0% or less, 4.0% or less, 3.0% or less, 2.0% or less, or 1% or less of the composite particles.

The oxytocin amount provided in a given inhaled dose of a pharmaceutical composition of such composite particles is sufficient to provide an approximately equal blood level achievable by the available intravenous or intramuscular administration. Thus, oxytocin is formulated to deliver in a given treatment, a systemic exposure equivalent to the 10 IU (~20 mcg) oxytocin intramuscular injection product.

Depending upon factors including, but not limited to, the systemic bioavailability of the intramuscular injection, the deposition performance of the inhaled pharmaceutical composition, and bioavailability of the inhaled dose, certain embodiments of the pharmaceutical composition of the present invention may contain from about 10 mcg and 800 mcg of oxytocin. Further suitable ranges may be selected from an inhaled dosage of about 25 to 600 mcg. Still further selected ranges include from 50 to 400 mcg oxytocin.

For example, if one assumes, pending clinical data, that intramuscularly injected oxytocin is, e.g., 50% or less systemically bioavailable, and in vitro cascade impaction data suggested that ~20% of the nominal dose of an inhaled product is deposited in regions of the lung from where systemic absorption can occur, the equivalent inhaled dose is predicted to be 50 to 400 mcg, where the systemic bioavailability of deposited lung dose lies in the range of 25% to 200% of the assumed intramuscular bioavailability.

In such circumstances, a 200 mcg dose reflects a lung bioavailability which is 50% of that of intramuscular bioavailability.

In this further aspect of the invention, the divalent cation material comprises a material providing divalent cations, such as $Be^{2+}$, $Ca^{2+}$, $Mg^{2+}$, $Sr^{2+}$, $Ba^{2+}$, $Ra^{2+}$, $Fe^{2+}$, $Zn^{2+}$ and/or $Cu^{2+}$. The divalent cationic material may be presented in any suitable form, such as a suitable salt, etc., which is soluble, allows dissociation of the divalent cation, and which is pharmaceutically acceptable.

In one or more embodiments, the divalent cationic material comprises, consists essentially of, or consists of a $Ca^{2+}$ providing material. In various embodiments, the divalent cationic material is in the form of a salt. Examples of such salts include a calcium salt, such as calcium lactate, calcium sulfate, calcium citrate, calcium chloride, calcium acetate or any combination thereof.

In the various embodiments, the divalent cationic material is present at an chemically stabilizing amount, which is believed to be a molar ratio of divalent cationic material to polypeptide of greater than or equal to (≥) 1:1, such as independently, ≥2:1, ≥3:1, ≥4:1, ≥5:1, ≥6:1, ≥7:1, ≥8:1, ≥9:1, ≥10:1, ≥15:1, ≥20:1, ≥25:1, ≥50:1. The amount of divalent cationic material should not be so great as to adversely impact the physical stability or aerosolization performance of the composite particles.

In specific embodiments, the divalent cation material is present in an amount less than 5 molar equivalents to the amount of oxytocin, such as 4.75 molar equivalents or less, 4.5 molar equivalents or less, 4.25 molar equivalents or less, 4.0 molar equivalents or less, 3.75 molar equivalents or less, 3.5 molar equivalents or less, 3.25 molar equivalents or less, 3.0 molar equivalents or less.

The divalent cation material is present in any suitable amount. In certain embodiments, the divalent cationic material (salt) comprises 5.0% or less of the w/w composite particle. Thus, in such embodiments, the divalent cationic material comprises independently, 5.0% w/w or less, 4.5% w/w or less, 4% w/w or less, 3.5% w/w or less, 3% w/w or less, 2.5% w/w or less, 2.0% w/w or less, 1.5% w/w or less, or 1% or less, 0.75% w/w or less, 0.5% w/w or less, 0.25% w/w or less, 0.1% w/w or less, 0.01% w/w or less of the composite particles, the amount dependant on the amount of disulfide bridge-closed ring-bearing polypeptide present.

The carbohydrate component of the composite particles, may comprise, either alone or any combination, disaccharides (e.g., trehalose, sucrose, and the like); cyclodextrins (e.g., 2-hydroxypropyl-β-cyclodextrin, etc.); polysaccharides (e.g., Inulin, raffinose, maltodextrins, dextrans, and the like), and/or sugar alcohols (e.g., mannitol and sorbitol, and the like). Non-reducing sugars and sugar alcohols are preferred, as reducing sugars may increase impurity formation, such as adduct formation, in the polypeptide component. In one or more preferred embodiments, said carbohydrate comprises, consists, or consists essentially of trehalose.

The carbohydrate generally acts as a water replacer and glassy stabiliser in spray dried protein formulations. The composite particles should make up a sufficient percentage of the particle to prevent aggregation of the polypeptide on spray drying and storage, such as from 10% to 90% w/w composite particles, e.g., 25%-80% w/w composite particles. Thus, in certain embodiments, the carbohydrate component of the composite particles comprises, independently, 90% w/w or less, 85% w/w or less, 80% w/w or less, 75% w/w or less, 70% w/w or less, 65% w/w or less, 60% w/w or less, 55% w/w or less, 50% w/w or less, 45% w/w or less, 40% w/w or less, 35% w/w or less, 30% w/w or less, 25% w/w or less, 20% w/w or less, 15% w/w or less, or 10% w/w or less of the composite particles.

The amino acid component of the composite particles, which acts as a hydrophobic shell former, may comprise, either alone or any combination, amino acids such as glycine, alanine, aspartic acid valine, leucine, isoleucine, methionine, proline, phenylalanine, trytophan, serine, threonine, cysteine, tyrosine, asparagine, glutamic acid, lysine, arginine, histidine, norleucine, and modified forms thereof. Amino acids, as used in this context, include di- and tri-peptides of the amino acids glycine, alanine, valine, leucine, isoleucine, methionine, proline, phenylalanine, trytophan, serine, threonine, cysteine, tyrosine, asparagine, glutamic acid, lysine, arginine, histidine, norleucine (including, but not limited to trileucine). In certain embodiments, for di-leucyl containing trimers, the third amino acid component of the trimer may be one of the following leucine (leu), valine (val), isoleucine (isoleu), tryptophan (try) alanine (ala), methionine (met), phenylalanine (phe), tyrosine (tyr), histidine (his), and proline (pro). "Leucine", whether present as a single amino acid or as an amino acid component of a peptide, refers to the amino acid leucine, which may be a racemic mixture or in either its D- or L-form. In one or more particular embodiments of the invention, the one or more amino acid of the composite particles, comprises, consists essentially of, or consists of L-leucine.

In one aspect of the invention, the amino acid, hydrophobic shell-forming component may comprise 40.0% or less or the composite particle mass. Thus, the hydrophobic shell forming material may be independently, 40% w/w or less, 35% w/w or less, 30% w/w or less, 25% w/w or less, 20% w/w or less, 15% w/w or less, or 10% w/w or less of the composite particles. In further embodiments, the hydrophobic shell-forming component makes up about from about 40% to 10% of the composite particles, for example, from about 25.0% to 15.0% of the composite particles. In certain embodiments, the hydrophobic shell-forming component comprises from about 22% to about 18% of the composite particles, e.g., about 20.0% the composite particles.

The composite particles may comprise the sole content of a formulation delivered by a dry powder inhaler, or as described below, formulated in a pressurized liquid propellant formulation and delivered via an MDI. Alternatively, the composite particles described herein may be formed as a pharmaceutical formulation which further comprises dry powder carrier/diluent particles of non-respirable sized, pharmaceutically acceptable excipient.

In a certain embodiments of the present invention, the composite particles may be admixed with a suitable carrier/diluent material fraction, which may be in the form of an amorphous powder, a crystalline powder, or a combination of amorphous and crystalline powders. Suitable carrier/diluent materials include:

(a) carbohydrates, including non-reducing sugars, such as disaccharides (e.g., trehalose, surcrose, and the like); cyclodextrins (e.g., 2-hydroxypropyl-β-cyclodextrin, etc.); and/or polysaccharides (e.g., inulin, raffinose, maltodextrins, dextrans, and the like); cyclodextrins (e.g., 2-hydroxypropyl-β-cyclodextrin);
(b) amino acids (e.g., glycine, arginine, aspartic acid, glutamic acid, cysteine, lysine, and the like);
(c) organic salts prepared from organic acids and bases (e.g., sodium citrate, sodium ascorbate, magnesium gluconate, sodium gluconate, tromethamine hydrochloride, and the like);
(d) peptides and proteins (e.g., aspartame, human serum albumin, gelatin, and the like); and/or
(e) alditols (e.g.; mannitol, xylitol, and the like), either individually or in any combination.

Lactose is disfavored as a carrier/diluent in the present formulation, as it reacts with oxytocin, via a malliard reaction on the terminal amino group of oxytocin, resulting in rapid impurity formation.

In certain embodiments, the carrier/diluent particles comprise, consist essentially of, or consist one or more alditols. In particularly preferred embodiments, the carrier/diluent particles comprise, consist essentially of, or consist of, mannitol.

The carrier/diluent particles may be manufactured, for example, formed by a milling from larger particles, or may be generated as appropriately sized particles, for example by spray drying.

The carrier/diluent particles are generally of non-respirable size. Within this aspect of the invention, suitable carrier/diluent particle compositions (without additive material) have MMAD) of greater (>) than 10 microns in size. For example, the carrier/diluent fraction has a MMAD of greater than 10 μm to about 500 μm, such as from >10 μm to 50 μm, from 50 μm-100 μm, from 100 μm-150 μm. In certain other embodiments, the MMAD of the carrier fraction is from greater than 35 μm to 100 μm.

In one or more embodiments of this aspect of the invention, the pharmaceutical formulation further comprise an additive material, wherein the additive material comprises one or more stearates, such as calcium stearate, magnesium stearate, and/or one or more amino acid, in any combination. In one or more particular embodiments, the additive material comprises, consists essentially of or consists of magnesium stearate.

In embodiments where an additive material is incorporated in the pharmaceutical formulation, the additive is generally 10% or less of the mass of the carrier/diluent fraction. In such embodiments, the additive material may combined with the carrier/diluent, and together form a carrier/diluent-additive blend. For example, blends within this aspect of the invention comprise, for example, independently, from about 99.75:0.25% w/w, about 99.50:0.50% w/w, about 99.25:0.75% w/w, about 99.0:1.0% w/w, about 98.75:1.25% w/w, about 98.50:1.50% w/w, about 98.25:1.75% w/w, about 98.0:2.0% w/w, about 97.75:2.25% w/w, about 97.50:2.50% w/w, about 97.25:2.75% w/w, about 97.0:3.0% w/w, about 96.75:3.25% w/w, about 96.50:3.50% w/w, about 96.25:3.75% w/w, about 96.0:4.0% w/w, about 95.75:4.25% w/w, about 95.50:4.5% w/w, about 95.25:4.75% w/w, about 95.0:5.0% w/w, about 94.75:5.25% w/w, about 94.50:5.5% w/w, about 94.25:5.75% w/w, about 94.0:6.0% w/w, about 93.75:6.25% w/w, about 93.50:6.5% w/w, about 93.25:6.75% w/w, 93.0:7.0% w/w, about 92.75:7.25% w/w, about 92.50:7.5% w/w, about 92.25:7.75% w/w, 92.0:8.0% w/w, about 91.75:8.25% w/w, about 91.50:8.5% w/w, about 91.25:8.75% w/w, 91.0:9.0% w/w, about 90.75:9.25% w/w, about 90.50:9.5% w/w, about 90.25:9.75% w/w, or 90.0:10.0% w/w carrier/diluent mass:additive material mass.

The particles of additive material may be of respirable or non-respirable size range. In certain embodiments, the additive fraction particles have an MMD prior to admixing with one or more other component particles of the composition (i.e., with carrier/diluent particles fraction, or the combined carrier/diluent and composite particles, or with the composite particle fraction) of 100 μm or less, such as, independently, 95 μm or less, 90 μm or less, 85 μm or less, 80 μm or less, 75 μm or less, 70 μm or less, 60 μm or less, 50 μm or less, 40 μm or less, 30 μm or less, 20 μm or less, or 10 μm or less. In still other further embodiments, the additive material fraction comprises additive material particles having an average particle size (e.g. Mean Mass Diameter) of, independently, 10 μm or less, for example, 9 μm or less, 8 μm or less, 7 μm or less, 6 μm or less, 5 μm or less, 4 μm of less, 3 μm or less, 2 μm or less, or 1 micron or less.

In embodiments where the pharmaceutical formulation comprises the composite particles, the carrier/diluent carrier particles, and the additive material, these components may be admixed in any suitable manner, as would be recognized by those of ordinary skill. For example, the additive material may be admixed with the carrier/diluent particles to form a carrier/diluent-additive pre-blend. The pre-blend may then admixed with the composite particles containing the therapeutically active polypeptide (e.g. oxytocin).

Alternatively, the additive material may be admixed with the composite particles, and then the admixed composite particle-additive material may then be admixed with the carrier diluent particles.

Still alternatively, the composite particles, the carrier/diluent particles and additive material can be mixed simultaneously.

Mixing of the materials may occur by any suitable fashion, including high shear milling, mechanofusion, ultracentrifugal milling, jet milling, high pressure homogenisation, ball milling, agitator bead milling, air jet milling, pin milling, hammer milling or knife milling, resonant acoustic mixing or other suitable process/mechanism.

The carrier/diluent material may be combined with the additive material, for example, the materials of both could be co-spray dried from one or more solution or suspension feedstock(s) to generate carrier/diluent particles containing the additive material.

The blend strength, i.e., the percentage of composite particles vs. the percentage of the carrier/diluent fraction (which can be with or without additive) in the total mass of dry powder may be used to control the dose of oxytocin delivered in a single inhalation. The blend strength will be determined by consideration of such factors as the percentage of of oxytocin in the composite particles, the amount of the composite particles needed to achieve a given dosage, and the fill weight of a given dose container (e.g., blister or capsule).

Thus, in embodiments where the composite particles are admixed or blended with carrier/diluent (with or without additive material) particles, the ratio of the fraction of the active-containing (composite) to the inactive containing (carrier/diluent (with or without additive material) may be from 0.001:99.999 to 99.999. In the embodiments described herein, the percentage of composite particles in the dry powder pharmaceutical composition may comprise, independently, for example, greater than (>) 0.001%, >0.01%, >0.1%, >1.0%, >2.0%, >3%, >4%, >5.0%, >6%, >7%, >8%, >9%, >10%, >11%, >12%, >13%, >14%, >15%, >16%, >17%, >18%, >19%, >20%, >21%, >22%, >23%, >24%, >25%, >26%, >27%, >28%, >29%, >30%, >31%, >32%, >33%, >34%, >35%, >36%, >37%, >38%, >39%, >40%, >41%, >42%, >43%, >44%, >45%, >46%, >47%, >48%, >49%, >50%, >51%, >52%, >53%, >54%, >55%, >56%, >57%, >58%, >59%, >60%, >61%, >62%, >63%, >64%, >65%, >66%, >67%, >68%, >69%, >70%, >71%, >72%, >73%, >74%, >75%, >76%, >77%, >78%, >79%, >80%, >81%, >82%, >83%, >84%, >85%, >86%, >87%, >88%, >89%, >90%, >91%, >92%, >93%, >94%, >95%, >96%, >97%, >98%, or >99% of the pharmaceutical composition.

Thus, in certain embodiments of the present invention, the invention provides a pharmaceutical formulation comprising:
  (a) a plurality of composite particles, each of said composite particles comprising, consisting, or consisting essentially of:
    (i) pharmacologically effective amount of oxytocin,
    (ii) a molar equivalent amount or greater, to the amount of oxytocin, of a divalent cationic material comprising $Ca^{2+}$,
    (iii) carbohydrate, said carbohydrate comprising trehalose, and
    (iv) amino acid, L-leucine,
  wherein the composite particles have a MMAD of about 5 μm to about 0.5 μm,
  (b) carrier/diluent particles of non-respirable size, said carrier/diluent particles comprising mannitol; and
  (c) an admixed amount of magnesium stearate.

In a still further aspect of the present invention, the invention provides a method of making composite particles for use in a pharmaceutical formulation, comprising:
  (a) dissolving and/or suspending
    (i) an amount of reversible ring-bearing polypeptide (e.g., vassopressin or oxytocin),
    (ii) a molar equivalent amount or greater of a divalent cationic material to the amount of reversible ring-bearing polypeptide,
    (iii) amino acid, and
    (iv) carbohydrate
  in an pharmaceutically acceptable liquid to form a feedstock; and
  (2) removing the liquid from the feedstock to produce particles.
wherein the particles have a mass median aerodynamic diameter from about 0.5 μm to about 7 μm.

In another embodiment, the step of removing the liquid is achieved by spray drying, freeze drying, or the like.

It is a still further aspect of the present invention to provide a method of treating a condition treatable by oxytocin by the systemic delivery of oxytocin through the lung (e.g., post partum hemorrhage), comprising the steps of:
  (a) providing an inhaler containing at least one dose of a pharmaceutical formulation comprising: a plurality of composite particles in dry powder form, said composite particulars comprising: oxytocin, at least a one molar equivalent amount of a divalent cation to said oxytocin, amino acid, and carbohydrate.
  (b) dispersing said composite particles through activation said inhaler,
  (c) delivering said composite particles to the alveolar region of an individual's lung via inhalation to achieve systemic absorption.

It would be particularly desirable if such methods and compositions were sufficiently convenient to permit self-administration even away from hospital, or from medical staff, and were able to deliver a desired total dosage with a relatively low number of inhalations, preferably fewer than ten, more preferably fewer than 4, even more preferably 2, and most preferably or 1 inhalations.

A further understanding of the nature and advantages of the invention will become apparent by reference to the remaining portions of the specification and drawings.

DETAILED DESCRIPTION OF THE SPECIFIC EMBODIMENTS OF THE INVENTION

Figure 1:
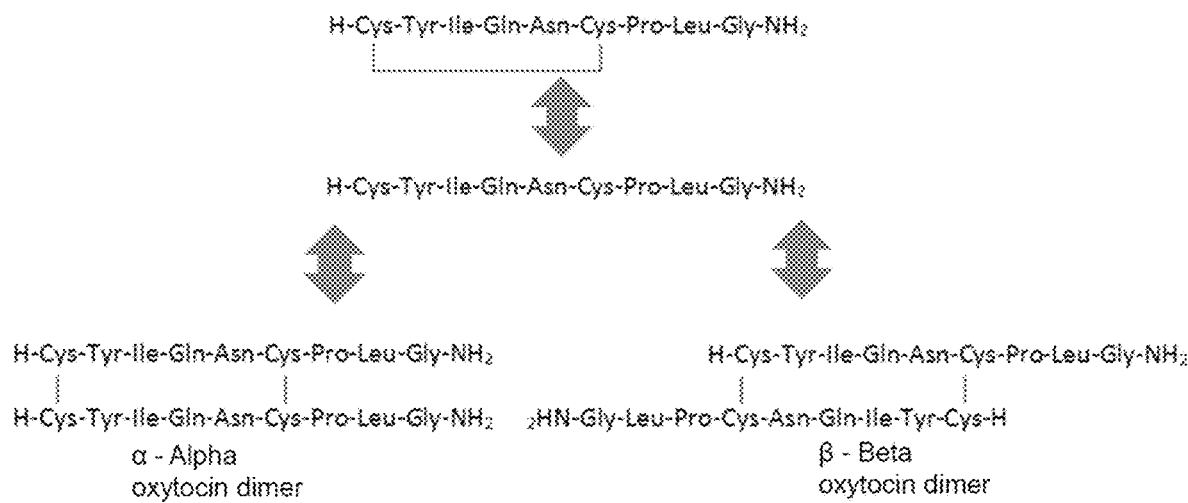
FIG. 1 is a schematic illustration of the reversible processes by which oxytocin, transforms from its cysteine-cysteine linked (disulfide bridge) ring orientation, to a linear form, to the formation of the α-dimer and β-dimer of oxytocin.

The following terms are used in the application and are intended to have the meaning indicated.

"Aqueous", as used in the context of a feedstock for particle production, will be understood to refer to a liquid which is constituted at least in part by water, but may include other water-miscible liquids, for example, which act as co-solvents, such as an alcohol (e.g., ethanol, isopropanol). In any event, the skilled person will recognize that the aqueous liquid must be suitable for spray drying according to the methods of the invention.

"Dry powder" refers to a powder composition that typically contains less than about 10% moisture, preferably less than about 6% moisture, and most preferably contains less than about 3% moisture, depending upon the particular formulation. By "powder," it is meant that the material comprises free flowing particulates having a size selected to permit penetration into the alveoli of the lungs, preferably being less than 10 μm in diameter, preferably less than 7 μm, and most preferably less than 5 μm, and preferably in the range from 5 μm to 0.5 μm in diameter.

"Fine Particle Mass" or "FPM" as used herein refers to mass of particles which deposit in stages 3, 4, and 5 of an NGI cascade impaction, which roughly equate to those particles aerodynamically sized from about 5 μm to about 1 micron, at a flow rate of 60 liters per minute. According to the product brochure for the NGI, stage 3 collects particles aerodynamically sized from 4.4 μm to 2.8 μm, stage 4 collects particles from 2.8 μm to 1.7 μm, and stage 5 collects particles from 1.7 μm to 0.92 μm.

"Mass median diameter" or "MMD" is a measure of mean particle geometric size, since the composite particles of the pharmaceutical compositions of invention may be polydisperse (i.e., consist of a range of particle sizes), or may fracture or agglomerate. MMD values as reported herein may be determined by laser diffraction, although any number of commonly employed techniques can be used for measuring mean particle size (e.g., electron microscopy, light scattering, laser diffraction). MMD values for, for example, the composite particles described herein, may be determined prior to blending with carrier/diluent particles.

"Mass median aerodynamic diameter" or "MMAD" is a measure of the aerodynamic size of dispersed particles. The aerodynamic diameter is used to describe an aerosolized powder in terms of its settling behavior, and is the diameter of a unit density sphere having the same settling velocity, in air, as the particle. The aerodynamic diameter encompasses particle shape, density and physical size of a particle. As used herein, MMAD refers to the midpoint or median of the aerodynamic particle size distribution of an aerosolized powder determined by cascade impaction, preferably by NGI, unless otherwise indicated.

"Next Generation Impactor (NGI)" refers to a cascade impactor for classifying aerosol particle into size fractions based on their deposition behavior, which contains seven impaction stages plus a final micro-orifice collector, and which is commercially available, for example, from MSP Corporation (Shoreline, Minn., USA). The impactor is described, for example in U.S. Pat. Nos. 6,453,758, 6,543, 301, and 6,595,368; UK Patent GB2351155, GB2371001, and GB2371247, and its application to inhalers is detailed in US Pharmacopeia 29: 601, "Aerosols, Nasal Sprays, Metered-Dose Inhalers, And Dry Powder Inhalers."

"Non-respirable sized" means particles having an aerodynamic size greater than 10 μm, such as greater than about 20 μm, for example greater 35 than μm, in some embodiments greater than 50 μm. Generally, such non-respirable particles for use as carrier/diluent materials in the present application have an MMAD between 15 and 500 μm in size.

"Pharmaceutically acceptable carrier/diluent" refers to excipient particles that may optionally be included in the compositions of the invention, and taken into the lungs with no significant adverse toxicological effects to the subject, and particularly to the lungs of the subject. Pharmaceutically acceptable carrier/diluent may include one or more additive excipient materials which improve the chemical or physical stability of the pharmaceutical formulation. The carrier/diluent particles (with or without additive) may be referred to as "carrier fraction" or "carrier/diluent fraction" herein.

"Pharmacologically effective amount" or "physiologically effective amount of a bioactive agent" is the amount of an active agent present in an aerosolizable composition as described herein that is needed to provide a desired level of active agent in the bloodstream of a subject to be treated to give an anticipated physiological response when such composition is administered pulmonarily. The precise amount will depend upon numerous factors, e.g., the active agent, the activity of the composition, the delivery device employed, the physical characteristics of the composition, intended patient use (i.e., the number of doses administered per day), patient considerations, and the like, and can readily be determined by one skilled in the art, based upon the information provided herein.

All references to salts herein include anhydrous forms and all hydrated forms of the salt.

Abbreviations:
 "% w/w" percentage content by weight
 "a/a" area/area
 "$CaCl_2$" calcium chloride
 "$Ca^{2+}$" the divalent calcium cation
 "CS" chemical stability
 "DSC" differential scanning calorimetry
 "FPF" fine particle fraction
 "HPLC" High pressure liquid chromatography
 "IM" Intramuscular
 "IU" International Unit
 "IV" Intravenous (IV)
 "KF" Karl Fischer
 "$Mg^{2+}$" the divalent magnesium cation
 "NGI" next generation impactor
 "T:L:O" trehalose:leucine:oxytocin in reference to % w/w "T:L:C:O" trehalose:leucine:CaCl2:oxytocin in reference to % w/w "UV" ultraviolet absorption "μm" microns or micrometers "WC" water content

DESCRIPTION OF THE VARIOUS EMBODIMENTS OF THE INVENTION

The present invention relates to reducing the formation of certain chemical degradants, such as dimer degradation products, associated with disulfide bridge-dosed ring-bearing polypeptides, such as of oxytocin, in an inhalable powder form, as well as processes for producing pharmaceutical compositions with improved chemical stability, the compositions themselves, as well as their use in therapy. Such compositions should also be physio-chemically stable, preferably consisting of a powder formulation, capable of withstanding heat and/or humidity for an appropriate period of time.

The main degradation pathway for oxytocin is well documented, as being the heat stimulated breakage of the disulfide bond of the two cysteine amino acids that form the cystine functionality within the oxytocin molecule. As seen in FIG. 1, oxytocin in the molecule's active form (top-most compound) forms a ring structure between the two cysteines, which are the first and sixth amino acids in the sequence. The ring is breakable, however, and once broken (as depicted by the middle compound), this bond can be re-formed either back into the active form of the molecule (as represented by the reversible arrow between the top and middle compounds), or as one of the two main degradants in the current commercial product, either the alpha-dimer or the beta-dimer, (as shown at the bottom of FIG. 1), either of which may be formed when this bond reforms with the cystine of another adjacent oxytocin molecule, rather than reforming within the same molecule.

Figure 2:
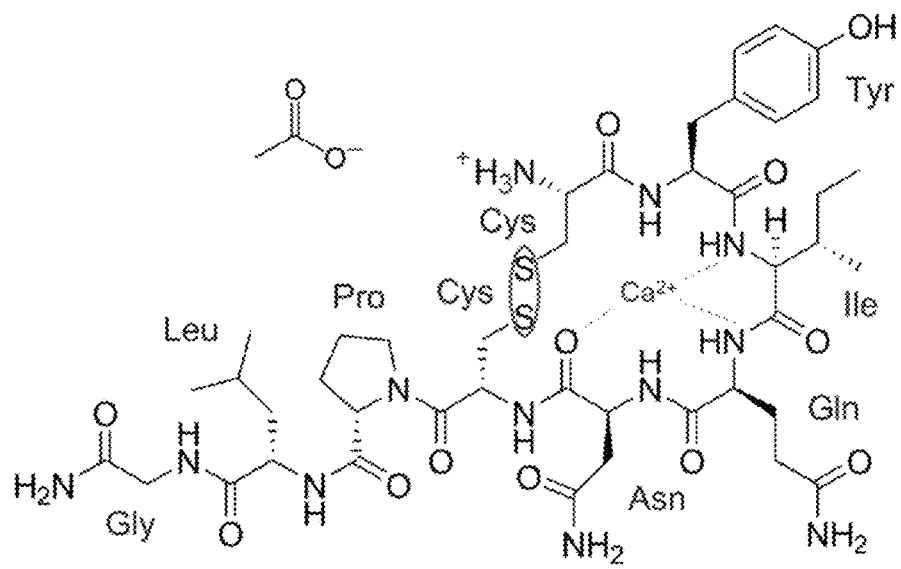
FIG. 2 is a schematic illustration of oxytocin, showing the interaction cysteine-cysteine disulfide bridge, which leads to formation of a ring structure, and the theorized functioning of a divalent cation position to stabilized the disulfide bridge in a solid state, according to the method of the present invention.

It is believed that the ring structure of the active form might contain sufficient polar groups in a suitable arrangement to form a complex around a central positively charged atom, and that such a positively charged atom might restrict the extent to which the oxytocin ring structure was able to open once the disulfide bond was broken. This arrangement is shown in FIG. 2, which depicts a divalent cation (e.g., $Ca^{2+}$, $Mg^{2+}$) situated within the ring structure. If this ring structure is preserved long enough for the bond to reform without the ring structure opening, the original active form of the molecule would be restored. In the solution phase, this benefit is likely to be minimal since all of the components are mobile; anything other than a very strong complex would be transient and still allow time for ring opening. However, in a solid phase matrix where the metal ion cannot escape the complex, it would provide a lasting ring holding and stabilising effect.

As described herein, an aspect of the invention provides a method for increasing physiochemical stability (e.g., by reducing the amount of dimer degradants) of a disulfide bridge-dosed ring-bearing polypeptide solid state composition (e.g., oxytocin) comprising the providing of at least a molar equivalent amount of divalent cation to the amount of oxytocin in a solid-phase. In certain embodiments, the divalent cationic material to polypeptide molar ratio is from 1:1 to 50:1. In specific embodiments, the divalent cationic material to polypeptide molar ratio is 1:1 to less than 5:1.

In certain embodiments of this method, the divalent cationic material provides, for example, $Ca^{2+}$, $Mg^{2+}$, $Fe^{2+}$, $Zn^{2+}$ and/or $Cu^{2+}$, for example in the form of a suitable salt. (e.g. $CaCl_2$, etc.). In such method, a suitable carbohydrate (e.g., trehalose) and/or hydrophobic amino acid (e.g., L-leucine) may be included in the said solid state composition, and discussed further herein.

As oxytocin is structurally similar to the vassopressins, for example, the amino acid sequence of arginine vasopressin is Cys-Tyr-Phe-Gln-Asn-Cys-Pro-Arg-Gly, with the cysteine residues forming a disulfide bond. Lysine vasopressin has a lysine in place of the arginine. The discussion herein is equally applicable to other compounds containing disulfide bridging bonds.

In a further aspect of the invention, oxytocin is present in a composite particle, further comprising a molar equivalent amount or greater of divalent cationic material, at least one amino add, and at least one carbohydrate excipient. The carbohydrate is believed to be beneficial in the composite particles, not only to act as a water replacer and structural component, but also acts to assist in increasing the likelihood of ring structure re-forming in preference to dimer formation, and to increase the glass transition temperature of (Tg) of the formulation.

The physiochemical stability may be measured, for example, in reduced formation of the amount of α (alpha)-oxytocin dimer and/or β (beta) oxytocin dimer in comparison to a dry powder formulation lacking such divalent cation.

In particular embodiments, the composite particles comprise oxytocin; the divalent cationic material, calcium chloride; the amino acid, L-leucine; and the carbohydrate, mannitol.

As described herein, a still further aspect of the invention to provide a pharmaceutical formulation comprising a plurality of composite particles, each of said composite particle comprising:

oxytocin, a molar equivalent amount or greater of one or more divalent cationic material, in relation to said oxytocin, amino acid, and carbohydrate, wherein said particles having an aerodynamic particle size from about 5 μm and 0.5 μm, and are suitable for delivery to the alveolar region of the lung.

In one or more embodiments of the various aspect of the invention, the selected excipients form an amorphous glass matrix in which the oxytocin is dispersed, which is substantially non-crystalline, or has no substantial regions of crystallinity or regular repeating structural molecular order.

In certain embodiments, amino acid content of the composite particles comprises L-leucine, and the L-leucine will represent between 5 and 40% by weight of the dry ingredients of the formulation. More preferably, the L-leucine will comprise between 10 and 40% by weight of the composite particles.

As will be appreciated, aerosolized particles deposit in the lung dependent upon aerodynamic factors, as well as on other factors such as density, air flow velocity and directionality, among others. Aerodynamically, the composite particles of the present invention are designed to be less than 7 μm, preferably less than 5 μm, but larger than about 0.5 μm in size. Thus, they are designed to deposit in the alveolar region of the patient's lungs. Thus, composite particles may be generated to have an aerodynamic size, independently, of less than 7 μm, more preferably less than about 6 μm, such as, independently, about 5 μm or less, about 4 μm or less, about 3 μm or less, about 2 μm or less, or about 1 μm to about 0.5 μm.

The pharmaceutical compositions of the present invention are intended for delivery to the lung and will possess a mass median aerodynamic diameter (MMAD) of less than about 7 μm, for example, from about 6 μm to about 0.5 μm. Thus, compositions of such composite particles may have a MMAD of less than, independently, about 7 μm, more preferably less than about 6 μm, such as, independently, about 5 μm or less, about 4 μm or less, about 3 μm or less, about 2 μm or less, or about 1 μm to about 0.5 μm.

Preferred compositions according to the present invention will be substantially free from penetration enhancers. "Penetration enhancers" are surface active compounds which promote penetration of oxytocin (or other drugs) through a mucosal membrane or lining and are proposed for use in intranasal, intrarectal, and intravaginal drug formulations. Exemplary penetration enhancers include bile salts, e.g., taurocholate, glycocholate, and deoxycholate; fusidates, e.g., taurohydrofusidate; and biocompatible detergents, e.g., Tweens, Laureth-9, and the like. The use of penetration enhancers in formulations for the lungs, however, is generally undesirable because the epithelial blood barrier in the lung can be adversely affected by such surface active compounds. In the case of oxytocin, it is believed to be desirable to avoid a material designed to accelerate oxytocin delivery to the blood, as most of the side effects associated oxytocin are associated with Cmax.

Oxytocin is a generally amorphous material. Dry powder oxytocin is preferably prepared by spray drying under conditions which result in a substantially amorphous powder having a particle size within the above-stated range. The preferred method for forming oxytocin powders comprising particulates in the desired size range is spray drying, where pure, bulk oxytocin acetate is dissolved in a solution containing the other excipients dissolved to give a total dissolved solids content of 5% w/w. If required, the pH of the solution may be adjusted. The solution may then be spray dried in conventional spray-drying equipment from commercial suppliers, such as Buchi, Niro, and the like, resulting in a substantially amorphous particulate product.

The oxytocin powders of the present invention may optionally be combined with pharmaceutical carriers or excipients which are suitable for respiratory and pulmonary administration. Such carriers may serve simply as bulking agents when it is desired to reduce the oxytocin concentration in the powder which is being delivered to a patient, but may also serve to enhance the stability of the oxytocin compositions and to improve the dispersibility of the powder within a powder dispersion device in order to provide more efficient and reproducible delivery of the oxytocin and to improve handling characteristics of the oxytocin such as flowability and consistency to facilitate manufacturing and powder filling.

Suitable carrier/diluent materials may be in the form of an amorphous powder, a crystalline powder, or a combination of amorphous and crystalline powders. Suitable materials include carbohydrates, non-reducing sugars, such as disaccharides, such as trehalose, sucrose, and the like; cyclodextrins, such as 2-hydroxypropyl-β-cyclodextrin; and polysaccharides, such as raffinose, maltodextrins, dextrans, and the like; (b) amino acids, such as glycine, arginine, aspartic acid, glutamic acid, cysteine, lysine, and the like; (c) organic salts prepared from organic acids and bases, such as sodium citrate, sodium ascorbate, magnesium gluconate, sodium gluconate, tromethamine hydrochloride, and the like; (d) peptides and proteins, such as aspartame, human serum albumin, gelatin, and the like; (e) alditols, such as mannitol, xylitol, and the like. In one or more embodiments, the carrier/diluent particles include alditiols, (e.g., mannitol). Lactose is disfavored as a carrier/diluent in the present formulation, as it reacts with oxytocin, resulting in rapid impurity formation.

The carriers may be separately prepared in a dry powder form and combined with the dry powder oxytocin by blending. The separately prepared powder carriers will usually be crystalline (to avoid water absorption), but might in some cases be amorphous or mixtures of crystalline and amorphous. The size of the carrier particles may be selected to improve the flowability of the plurality of composite particles; typically such carrier particles being in the range from 25 μm to 200 μm. Carrier particles in this size range will generally not penetrate into the alveolar region of the lung and will often separate from the oxytocin in the delivery device prior to inhalation. Thus, the particles which penetrate into the alveolar region of the lung will consist essentially of selected active pharmaceutical ingredient, (e.g., oxytocin), a chemically stabilizing amount of a divalent cation which is present in a molar equivalent of greater amount to the oxytocin, as well as an amino acid and carbohydrate. A preferred carrier/diluent material is crystalline mannitol having a size in the above-stated range. In further embodiment, the carrier/diluent particles are admixed with an additive material (e.g., magnesium stearate).

The particles comprising the carrier/diluent fraction are, in certain embodiments, of non-respirable size. Such carrier/diluent fraction can be formed within a controlled range of sizes in order to impart a desired characteristic or attribute upon the pharmaceutical formulation. For example, the diluent/carrier fraction may comprise particles aerodynamically sized between a lower and an upper limit. Suitable ranges may be independently selected, for example, as falling within the range from greater than (>)10 μm to 500 μm, >10 μm to 400 μm, >10 μm to 300 μm, >10 μm to 200 μm, >10 μm to 100 μm, >10 μm to 50 μm, 20 μm to 500 μm, 20 μm to 400 μm, 20 μm to 300 μm, 20 μm to 200 μm, 20 μm to 100 μm, 20 μm to 50 μm, 30 μm to 500 μm, 30 μm to 400 μm, 30 μm to 300 μm, 30 μm to 100 μm, 30 μm to 50 μm, 35 μm to 500 μm; 35 μm to 400 μm, 35 μm to 300 μm, 35 μm to 200 μm, 35 μm to 100 μm, 35 μm to 50 μm, 40 μm to 500 μm; 40 μm to 400 μm, 40 μm to 300 μm, 40 μm to 200 μm, 40 μm to 100 μm; 40 μm to 50 μm, 45 μm to 500 μm; 45 μm to 400 μm, 45 μm to 300 μm, 45 μm to 200 μm, 45 μm to 100 μm; 45 μm to 50 μm, 50 μm to 500 μm, 50 μm to 400 μm, 50 μm to 300 μm, 50 μm to 200 μm, 50 μm to 100 μm; 60 μm to 500 μm, 60 μm to 400 μm, 60 μm to 300 μm, 60 μm to 200 μm, 60 μm to 100 μm; 75 μm to 500 μm, 75 μm to 400 μm, μm to 300 μm, 75 μm to 200 μm, 75 μm to 100 μm; 100 μm to 500 μm, 100 μm to 400 μm, 100 μm to 300 μm, 100 μm to 200 μm, 150 μm to 500 μm, 150 μm to 400 μm, 150 μm to 300 μm, 150 μm to 200 μm, 200 μm to 500 μm, 200 μm to 400 μm, and 200 μm to 300 μm, 250 μm to 500 μm, 250 μm to 400 μm, and 250 μm to 300 μm, 300 μm to 500 μm, 300 μm to 400 μm, 350 μm to 500 μm, 350 μm to 400 μm, and 400 μm to 500 μm, and suitable ranges between the forgoing individual subsets of ranges.

As mentioned above, the oxytocin containing pharmaceutical formulations of the present invention are preferably arranged so that each inhaled dose equates to a blood level achievable intravenously or intramuscularly. Thus, oxytocin is formulated to deliver in a single inhaled dose, systemic exposure equivalent to the 10 IU (~20 mcg) oxytocin intramuscular injection product.

The amount of active close-ring bearing polypeptide to be delivered or contained in a given dose in the various aspects of the instant application, depend upon on such factors as the systemic bioavailability of the peptide, the percentage of the nominal dose of inhaled composite particles delivered to the desired area within the lung, and the fill weight of the given dose container (e.g., capsule, blisyter, metered dose, etc.), all of which may be determined by those of ordinary skill.

In alternative embodiments, administration may be once daily, or several times daily, for example 2, 3, 4 or 8 times, giving for example 1 or more doses each time to achieve the desired blood level.

The administration time for delivering the dose is preferably less than 2 minutes, depending on the presentation, generally less than 30 seconds, preferably less than 20 seconds.

Pharmaceutical formulations may be presented in a dry powder form via a dry powder inhaler, or formulated as a suspension in a suitable pressurized liquid propellant and delivered via a metered dose inhaler.

Delivery Devices: Dry Powder Inhalers

The pharmaceutical compositions comprising a plurality of composite particles described herein may be metered into individual doses, and delivered in a number of ways, and additional aspects of the invention relate to dosage forms and inhalers of delivering metered quantities of the compositions of the present invention.

In such aspects, the composition of the present invention is in the form of a dry powder composition deliverable from a dry powder inhaler or as a pressurized liquid propellant suspension formulation delivered from a pressurized metered dose inhaler.

Thus, in one or more embodiments, the invention is directed to a dosage form adapted for administration to a patient by inhalation as a dry powder.

In one aspect of the present invention, we provide a dry powder inhaler which contains one or more pre-metered dose on the compositions of the present invention. "Dry powder inhaler" or "DPI" means a device containing one or more doses of the pharmaceutical composition of the present invention in dry powder form, a mechanism for exposing a dose of the dry powder into an air flow, and an outlet, in the form of a mouthpiece, through which a user may inhale to entrain the exposed dose of the pharmaceutical composition in the airflow and into the targeted region of the lung.

The pharmaceutical composition of the present invention may be contained within dose container containing a predetermined amount of the pharmaceutical composition. In one or more embodiments, the dose container may be a capsule or cartridge. For example, capsules may comprise hydroxypropyl methylcellulose, gelatin or plastic, or the like.

In certain embodiments, the capsule will have a powder capacity, for example, about 50 mg or less per capsule; e.g., 40 mg or less; 35 mg or less; 30 mg or less; 25 mg or less, or 20 mg or less per capsule, or other suitable amount. The degree to which the capsule is filled will be formulation in relation to the overall internal volume of the dose container (e.g. capsule, blister or metered dose) may be performance dependent, which is determinable by those of ordinary skill.

In a unit dose inhaler, the capsule/cartridges (one dose per capsule/cartridge) is generally loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ of GlaxoSmithKline (described for example in U.S. Pat. No. 4,353,365), the HANDIHALER™ of Boehringer Ingelheim, or the BREEZHALER™ of Novartis.

Multi-dose dry powder forms containing the pharmaceutical composition described herein may take a number of different forms. For instance, the multi-dose may comprises a series of sealed blistered with the composition sealingly contained in a blister pocket, and be arranged as a disk-shape or an elongate strip. Representative inhalation which use such multi-dose forms include devices such as the DISKHALER™, DISKUS™ and ELLIPTA™ inhalers marketed by GlaxoSmithKline. DISKHALER™ is described for example in U.S. Pat. Nos. 4,627,432 and 4,811,731. The DISKUS™ inhalation device is, for example, described in U.S. Pat. No. 5,873,360 (GB 2242134A). The ELLIPTA inhaler is described for example in U.S. Pat. Nos. 8,511,304, 8,161,968, and 8,746,242. Again, the dose containers (blisters, etc.) may be rupturable, peelable or otherwise openable one-at-a-time and the doses of the dry powder composition administered by inhalation on a mouthpiece of the inhalation device, as known in the art.

Alternatively, composition of the present invention may administered via a dry powder reservoir based, meter-in-device dry powder inhaler, wherein the pharmaceutical composition of the present invention is provided as a bulk in a reservoir of the inhaler. The inhaler includes a metering mechanism for metering an individual dose of the composition from the reservoir, which is exposed to an inhalation channel, where the metered dose is able to be inhaled by a patient inhaling at a mouthpiece of the device. Exemplary marketed devices of this type are TURBUHALER™ of AstraZeneca, TWISTHALER™ of Schering and CLICKHALER™ of Innovata.

In addition to delivery from passive devices, compositions of the present invention may be delivered from active devices, which utilize energy not derived from the patient's inspiratory effort to deliver and deagglomerate the dose of the composition.

The pharmaceutical composition may consist essentially of the composite particles described herein in dry powder form. Alternatively, the pharmaceutical composition may comprise the composite particles may admixed with a carrier/diluent particles, for example, mannitol, with or without further excipients materials (i.e., additives), such as lubricants, amino acids, or other excipients noted to have a beneficial properties in such carrier/diluent formulations, which combined form a finely divided powder.

In one or more embodiments of the present invention, the dry powder compositions of the invention have a moisture content below about 10% by weight water, such as a moisture content of about 9% or below; such as about 9, 8, 7, 6, 5, 4, 3, 2, or 1% or below by weight water. In one or more preferred embodiments, the dry powder pharmaceutical composition has a moisture content below about 3% by weight water, such as 1% or below. Moisture content may be determined by any suitable technique, such as volumetric titration and/or coulometric titration (e.g., Karl Fisher titration).

In various embodiments, the DPI dosage form, e.g., capsule or blisters, or DPI as a whole containing the pharmaceutical formulation, may also be used in conjunction with other structures such as, without limitation, overwrap packages for storing and containing the DPI or dosage form, with or without desiccant material or moisture content control material, which may be included therein as a sachet, or be integral to with the materials selected (i.e., the selected material has desiccant characteristics).

Delivery Devices: Metered Dose Inhalers

In a further aspect of the invention, the pharmaceutical composition described herein may be formulated in a suitable liquid pressurized liquid propellant, for use in a metered dose (MDI). "Metered dose inhaler" or "MDI" means a unit comprising a can, a secured cap covering the can and a formulation metering valve situated in the cap. MDI system includes a suitable channeling device. Suitable channeling devices comprise for example, a valve actuator and a cylindrical or cone-like passage through which medicament may be delivered from the filled canister via the metering valve to the nose or mouth of a patient such as a mouthpiece actuator. The pharmaceutical composition as detailed herein may be prepared as suspended particulates in the liquefied propellant for use in a MDI.

Thus, further aspects of the invention provide a metered dose inhaler containing a pharmaceutical formulation as described herein, as well as the liquid propellant pharmaceutical formulation for use therein itself. Such inhalers may be in the form of a metered dose inhaler (MDI) generally comprising a canister (e.g. an aluminum canister) closed with a valve (e.g. a metering valve) and fitted to an actuator, provided with a mouthpiece, and filled with a liquid pressurized liquid propellant formulation containing the pharmaceutical compositions as described herein. Examples of suitable devices include metered dose inhalers, such as the Evohaler® (GSK) such as Modulite® (Chiesi), SkyeFine™ and SkyeDry™ (SkyePharma).

When formulated for metered dose inhalers, the pharmaceutical compositions in accordance with the present invention are formulated as a suspension in a pressurized liquid propellant. In one or more embodiments of the present invention, while the propellant used in the MDI may be CFC-11, and/or CFC-12, although it is preferred that the propellant be an ozone friendly, non-CFC propellant, such as 1,1,1,2-tetrafluoroethane (HFC 134a), 1,1,1,2,3,3,3-heptafluoro-n-propane (HFC-227), HCFC-22 (difluorchloromethane), HFA-152 (difluoroethane and isobutene) either alone or in any combination.

Such formulations may be composed solely of propellant and the composite particles described herein, or alternatively may also include one or more surfactant materials, such as polyethylene glycol, diethylene glycol monoethyl ether, polyoxyethylene sorbitan monolaurate, polyoxyethylene sorbitan monooleate, propoxylated polyethylene glycol, and polyoxyethylene lauryl ether, oleic acid, lecithin or an oligolactic acid derivative e.g. as described in WO94/21229 and WO98/34596, for suspending the composition therein, and may also include agents for solubilising (co-solvents may include, e.g. ethanol), wetting and emulsifying components of the formulation, and/or for lubricating the valve components of the MDI, to improve solubility, or to improve taste. In one or more embodiments of the invention, the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™)

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminum can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations a metering valve is crimped onto an aluminum can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

The formulations of the invention may be prepared by dispersal of the composite particles of the pharmaceutical formulation in the selected propellant, with or without other components, in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by NGI, or other cascade impaction analytical process.

MDI canisters generally comprise a container capable of withstanding the vapour pressure of the propellant used such as a plastic or plastic-coated glass bottle or preferably a metal can, for example, aluminum or an alloy thereof which may optionally be anodized, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO96/32099). Preferably the canister is fitted with a cap assembly, wherein a drug-metering valve is situated in the cap, and said cap is crimped in place.

There is thus provided as a further aspect of the invention a pharmaceutical aerosol formulation comprising an amount of the composite particles as previously described and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

In a further embodiment, the invention is directed to a dosage form adapted for administration to a patient by inhalation via a metered dose inhaler.

In the case of suspension aerosol formulations, the particle size of the composite particles of oxytocin should be such as to permit inhalation of substantially all the drug into the lungs upon administration of the aerosol formulation, and will thus be less than desirably less than 10 µm, and in particular in the range of from 7 µm, such as from 0.5 to 5 µm, e.g., from about 1 to about 3 µm.

The following examples are offered by way of illustration, not by way of limitation.

EXPERIMENTAL 1

Materials and Methods Materials

Materials used are listed in Table 1

TABLE 1

| Materials | |
|---|---|
| Material | |
| Composite particles | |
| Oxytocin | 10% or less |
| Trehalose Dihydrate | Remainder |
| L-Leucine | 40% or less |
| Calcium chloride | Molar equivalent oxytocin or greater |
| Acetic acid | |
| Carrier/diluent-Additive Blend | |
| Mannitol | |
| Magnesium Stearate | |

Spray-dried particles may be produced by first creating a spray-dry feedstock solution, wherein: (1) formula quantities of excipients are weighed out; (2) a proportion of the purified water is added to the excipients and they are allowed to dissolve with agitation; (3) oxytocin is weighed according to formula, and added to the surface of the excipient solution and allowed to dissolve; (4) the remainder of the purified water is added to achieve the specified total weight; and (5) the pH of the solution is adjusted by adding acetic acid drop-wise to target pH 4.

The formulations are detailed in Table 2.

TABLE 2

| Spray-Dry Formulations | | |
|---|---|---|
| | Sample 1 (Control) | Sample 2 |
| Oxytocin (% w/w) | 5 | 5 |
| Oxytocin required amount (g) | 0.2790 | 0.2790 |
| Trehalose (% w/w) | 74.93 | 73.42 |
| Trehalose required amount (g) | 4.1404 | 4.0299 |
| Leucine (% w/w) | 20 | 20 |
| Leucine required amount (g) | 1.000 | 1.000 |
| $CaCl_2$ (% w/w) | n/a | 1.51 |
| $CaCl_2$ required amount (g) | n/a | 0.100 |

Spray Drying

Spray-dried formulations were produced using the SD Micro (GEA Niro). The spray drying parameters in Table 3 were used.

TABLE 1

| Spray Dry Parameters | |
|---|---|
| Parameter | Setting |
| Drying Gas flow (kg/hr) | 30 |
| Atomisation gas flow (kg/hr) | 5 |
| Inlet Temp (° C.) | 150 |
| Outlet Temp (° C.) | 70 |
| Solution Feed Rate (g/min) | Controlled to target outlet temperature (approx 12.5 g/min) |

Secondary Drying

Batches were prepared for secondary drying by removing the lid and replacing with a non-linting cleaning cloth which was secured in place with a cable tie around the neck of the jar.

Secondary drying was completed in the Gallenkamp Vacuum Oven (at ambient temperature). The E2M5 Edwards Vacuum pump (Asset PMP163070) and Buchi Vacuum controller (Biomax 65766) will be used to set a vacuum of below 5 mBar. The batches were held under vacuum for the recorded time.

Preparation of Carrier/Diluent-Additive Pre-Blend 99.0 g Mannitol (MMAD of 60 µm, with 10% of the particles less than 10% µm) was combined with 1.0 g. Magnesium Stearate (MgSt), to create a 99% carrier/diluent: 1% additive material mix. This was placed in a QMM blender, fitted with a blade and exposed to high shear blending (e.g. 10 minutes at 600 rpm) to obtain good mixing of components.

A Dry Powder Blend Formulation 8 g of the Carrier/diluent-Additive Preblend was combined with 2 g Composite Particles, to form 80/20 w/w % blends, as follows:

Turbula blending was conducted, using the following method: (1) Weigh out the required amounts of spray-dried composite particle formulation into 20 ml container; (2) Weigh out the required amount of Pre-blend (1% MgSt in Mannitol, previously manufactured on the QMM (high shear blender); (3) Add the pre-blend to the container; (4) Hand tumble for 30 sec.; (5) Secure the container; (6) Insert the container into the Turbula blender Jar using paper towels to pad the jar; and (7) Blend for 30 minutes at 42 rpm.

ANALYTICAL TESTING

1. Chemical Stability by HPLC: Oxytocin Drug-Related Impurities Content

Quantities of Sample 1 (control material) and Sample 2 (containing 1.5% $CaCl_2$) (both containing blended carrier/diluent with additive material) were placed in open glass vials, and the vials then housed under accelerated conditions (40° C./20% relative humidity (RH)). Portions of Sample materials were periodically checked, using Reverse Phase High Performance Liquid Chromatography, to determine α-oxytocin dimer and β-oxytocin dimer content.

The method for the determination of drug-related impurities content is performed by a reversed phase gradient HPLC method using the conditions presented below in Table 4.

TABLE 4

Chromatographic Conditions

| | |
|---|---|
| Analytical Column Details (column typoe, particle saize, and column dimensions) | Zorbax Bonus RP 3.5 μm 4.6 × 150 mm |
| Column Temperature | 60° C. |
| Mobile Phase A | 10 mM Ammonium formate in water |
| Mobile Phase B | 100% Acetonitrile |
| Flow Rate | 1.5 mL per minute |

| Gradient Profile | Time (mins) | % A | % B |
|---|---|---|---|
| | 0.0 | 90 | 10 |
| | 30 | 65 | 35 |
| | 35 | 20 | 80 |
| | 35.1 | 90 | 10 |
| | 40 | 90 | 10 |

| | |
|---|---|
| Detector Wavelength | 220 nm at Attenuation 2000 (for reporting) and 280 nm |
| Injection volume | 20 μl |
| Data collection time/reporting time | 40 mins |
| Run time | 40 mins |
| Autosampler wash solvent | Water |

Figure 3:
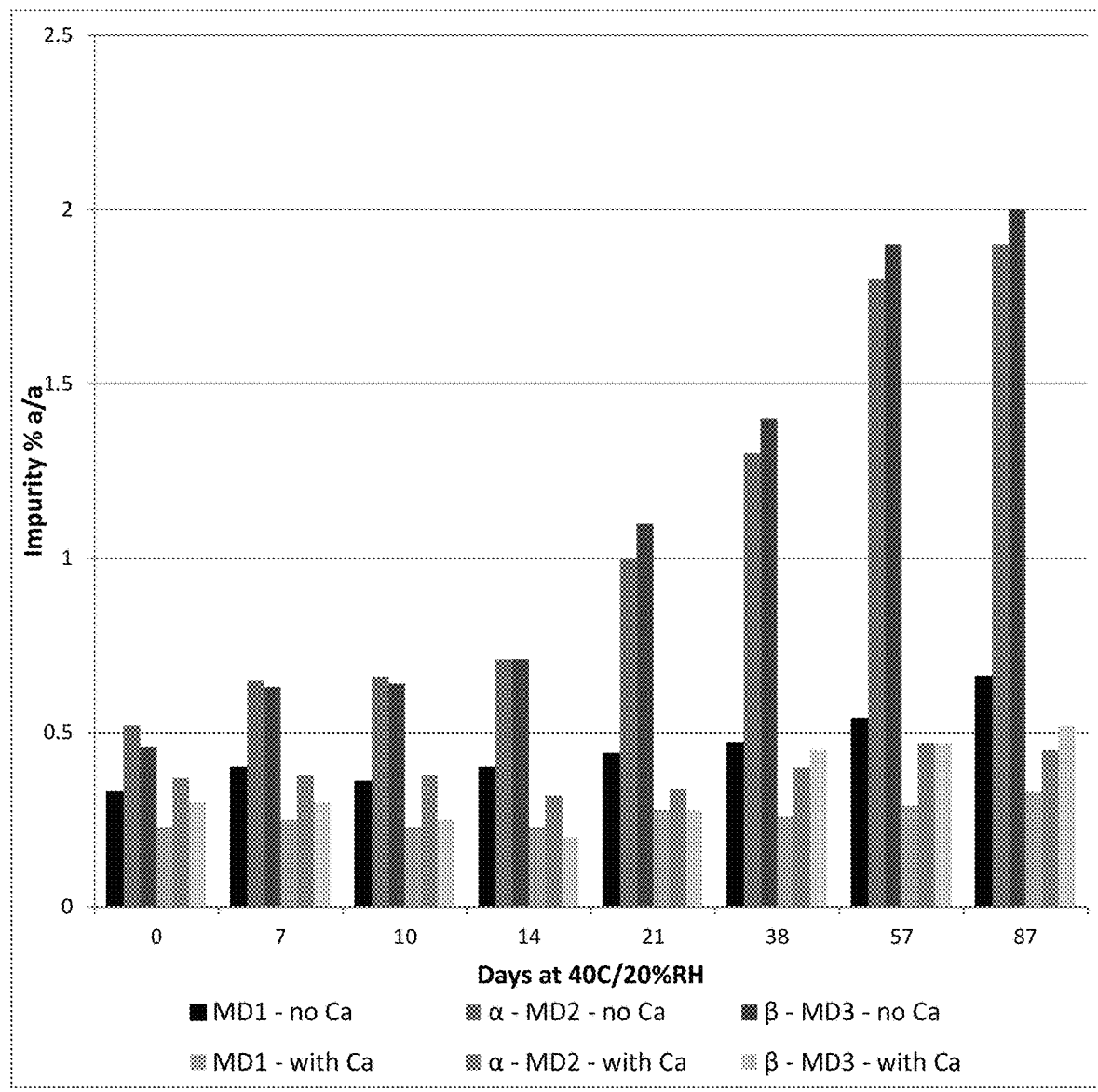
FIG. 3 is a graphic representation plotting % α-dimer (2nd and 4th bars for each of the days tested) and β-dimer (3rd and 6th bars on each of the days tesed) of oxytocin degradants over time in a forced degradation study comparing a pharmaceutical formulation of the present invention (with $CaCl_2$ (bars 4-6 for each day shown)) and a control (with no $CaCl_2$ (bars 1 to 3 for each day shown)).

The results of this HPLC study are shown in FIG. 3. As can be seen, the formation of both α-oxytocin dimer and β-oxytocin dimer is markedly greater in the control sample (Sample 1) than in Sample 2. Generally, in the control sample, the amount of both α-oxytocin dimer and β-oxytocin dimer in relation to total peptide content as determined by HPLA exceeded 0.5% of the of the total peptide content by day 7. The percentage of these impurities doubled in the control samples between day 0 and day 21, and approximately quadrupled from day 0 to day 87.

In comparison, Sample 2, containing the divalent dimer material, maintained low levels (~0.5% or below) of both α-oxytocin dimer and β-oxytocin dimer through the 87 day stability study.

2. Fine Particle Mass as Determined by NGI

Spray-dried composite particles were prepared by the methodology similar to that mentioned above, but without $CaCl_2$.

A portion of such particles underwent blending with the carrier/diluent particles+additive material (mannitol+magnesium stearate) and a portion of the spray dried materials was left unblended (i.e., samples lacked carrier/diluent+additive).

Samples of each of these portions materials were then subjected to FPM analysis using the NGI, operating at 60 l/min.

Figure 4:
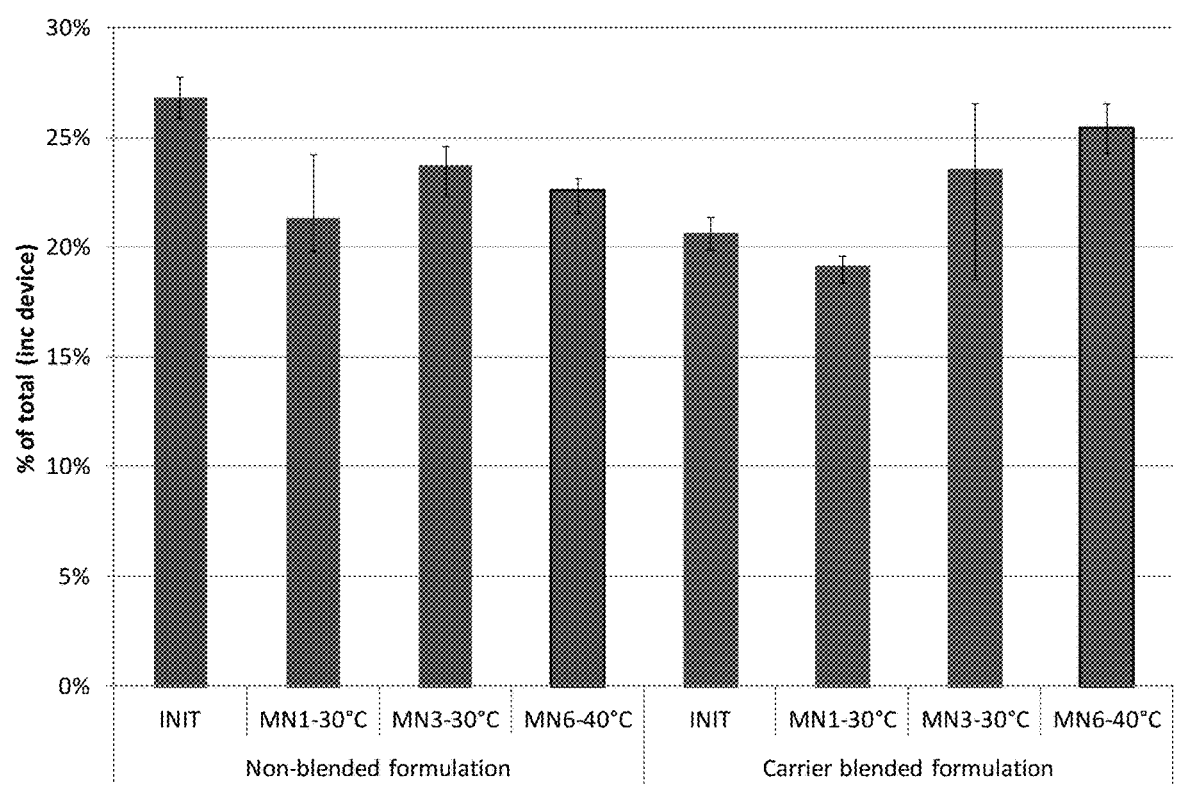
FIG. 4 is a graphic representation plotting FPM by NGI (n=3+/−max/min of individual values measured) of two pharmaceutical formulations of the present invention, one which had been blended with carrier/diluent particles and one which had not.

The results of such testing appear in FIG. 4. These results show FPM (i.e., stages 3, 4, and 5 of the NGI operated at 60 liters/min) remained relatively stable over a 6-month period of time when compared at 30, 90 and 180 days.

3. Moisture Content as Determined Using Karl Fisher Titration

Figure 5:
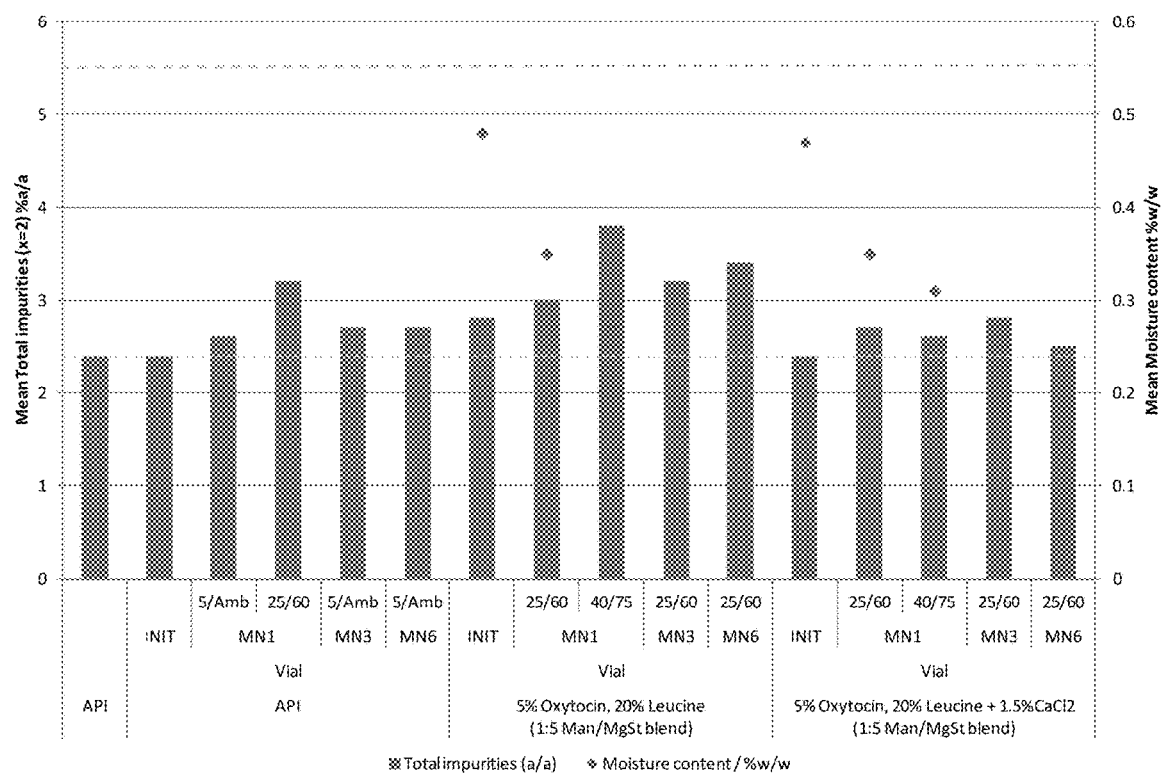
FIG. 5 is a graphic representation comparing total impurities and moisture content in bulk (freeze dried) oxytocin, a spray dried composite blend lacking a divalent cationic material, and a similar blend with 2% calcium chloride.

FIG. 5 shows total impurities and water content in bulk oxytocin, a spray dried composite blend lacking a divalent cationic material, and a similar composite blend with 2% calcium chloride. These results show that despite moisture content being approximately the same across the two blends at initial, 25° C./60% RH and 45° C./70% RH, that impurities were reduced in the 1.5% calcium chloride, in comparison with the control blend both at 25° C./60% RH and 45° C./70% RH.

EXPERIMENTAL II

Investigated the impact that the presence of the divalent cationic material (e.g., $CaCl_2$) in the composite particles has on the overall stability of the oxytocin component over time. Various amounts (0 to 4%) of divalent cationic material ($CaCl_2$) WAN oxytocin were prepared, and the samples of composite particles were then analysed for chemical degradation of the oxytocin. In these examples, the addition of an amount divalent cationic providing component ($CaCl_2$) was accompanied by a corresponding reduction in the amount of the carbohydrate component (trehalose) in the spray dried material.

Materials and Equipment:

TABLE 5

| Instrument | Details |
|---|---|
| ProCepT 4M8-TriX | Spray drying of formulations. |
| Perkin Elmer DSC 8500 | Measuring Tg by differential scanning calorimetry (DSC). |
| Metrohm Karl Fischer 890 Titrando | Directly measuring water content by Karl Fischer (KF) titration. |
| Shimadzu Prominence system | Assessing chemical degradation by HPLC. (Shimadzu prominence system comprising of a degasser (DGU 20A3), two pumps (LC 20AD), autosampler (SIL 20AHT), thermostatic column oven (CTO-20A), UV detector (SPD 20A) for solvent and sample delivery.) |
| Malvern Mastersizer | Particle size distribution |

Step 1: Manufacture

Formulations were manufactured using a ProCepT 4m8-TriX spray dryer (ProCepT nv, Zelzate, Belgium) each with identical spray drying conditions. The amount of $CaCl_2$ incorporated into the feed stock solution was varied. Utilising the data from the previous design of experiment study, the variable parameters for the driest formulation were used as shown below in Table 6. Additional constant parameters for these formulations included: feed stock solid content=5%, pH=4.0, cyclone air rate=0.15 $m^3 \cdot min^{-1}$, nozzle diameter=0.4 mm.

TABLE 6

| | Formulation parameters | | | | | |
|---|---|---|---|---|---|---|
| Formulation code | Composition/ Trehalose: Leucine: Oxytocin % w/w | $CaCl_2$ content/ % w/w | drying air rate/ $m^3min^{-1}$ | inlet temp./ °C | liquid feed rate/ $mL.min^{-1}$ | Actual yield/ % w/w |
| 1, 2 | 75.00:20:0.00:5 | 0.0 | 0.5 | 170 | 2.5 | 85, 86 |
| 3 | 74.98:20:0.02:5 | 0.02 | 0.5 | 170 | 2.5 | 86 |
| 4 | 74.80:20:0.20:5 | 0.2 | 0.5 | 170 | 2.5 | 87 |
| 5 | 74.00:20:1.00:5 | 1.0 | 0.5 | 170 | 2.5 | 88 |
| 6 | 73.00:20:2.00:5 | 2.0 | 0.5 | 170 | 2.5 | 88 |
| 7 | 71.00:20:4.00:5 | 4.0 | 0.5 | 170 | 2.5 | 88 |

After manufacture, the collection vessel was moved direct to a low humidity environment (<20% RH) and sealed. Samples were kept in a sealed bottle at 5° C. until analysis or transferred to vials for stability testing.

Step 2: Analysis

Each formulation was analysed immediately after manufacture for moisture content via Karl Fischer (KF). Glass transition Temperature (Tg) determined by differential scanning calorimetry (DSC). Particle size distribution (Mastersizer) and degradant content (by High pressure liquid chromatography (HPLC) as described above in the discussion of Experimentals I) were determined (as described in Table 9 below).

All formulations were dispensed into vials to be kept under accelerated and standard temperature conditions for 2 weeks, 1 month, 3 months and 6 months as detailed below.

Stability Protocol

The stability protocol used is shown below and is based on measurements of accelerated stability at 50° C. and at temperatures of 25° C. and 40° C., reflecting the ICH guideline values: Samples were stored in a fridge at 2-8° C., and in controlled ovens at either 25° C. and 40° C. in sealed (closed) conditions; Samples were stored in a 50° C. oven, in unsealed (open) containers at ambient humidity (approximately 10% RH); Samples were analysed for oxytocin and related substances content at time points defined by the schedule in Table 7 below.

TABLE 7

| | Stability Protocol | | | | |
|---|---|---|---|---|---|
| Condition T/° C.-RH | INIT | WK2 | MN1 | MN3 | MN6 |
| 2-8-Amb. (closed) | X | | | | X[1] |
| 25-Amb. (closed) | | | | | X[1] |
| 40-Amb. (closed) | | | | X | X[1] |
| 50-Amb. (open) | | X | X | | |

[1]To be analysed.

Results

Physical analysis (immediately post-manufacture)

Figure 6:
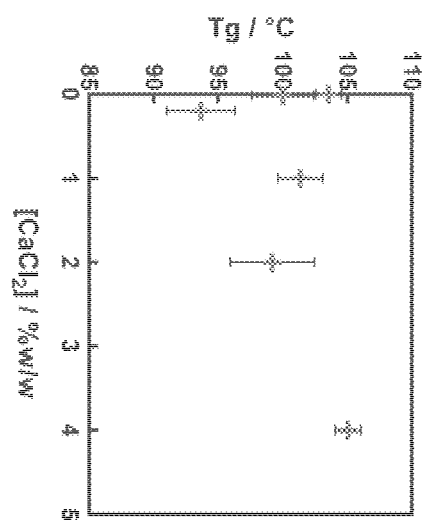
FIG. 6 is a graphic representation of the Glass Transition temperatures for composite particles containing 0%, 1%, 2,%, and 4% divalent cationic containing particle compositions.
Figure 7:
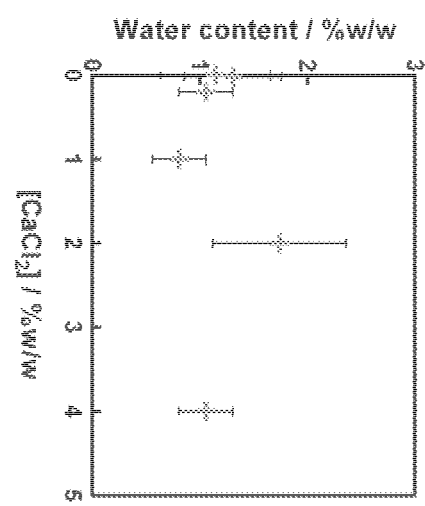
FIG. 7 is a graphic representation of the moisture content for composite particles containing 0%, 1%, 2%, and 4% divalent cationic material containing particle compositions.
Figure 8:
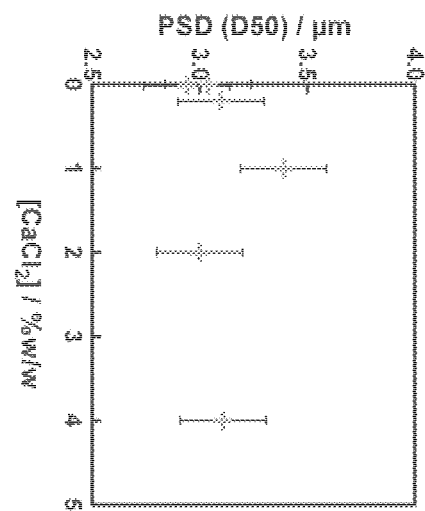
FIG. 8 is a graphic representation of the Particle Size distribution for composite particles containing 0%, % 2%, and 4% divalent cationic material containing particle compositions.

All formulations were analysed immediately after manufacture for glass transition temperature, moisture content and particle size distribution, to ensure minimal variability between samples. The graphs in FIG. 6 (Tg), FIG. 7 (moisture content) and FIG. 8 (Particle Size Distribution) below show the results for the parameters indicating no significant variation across all $CaCl_2$ concentrations, as reflected in Table 8 immediately below:

TABLE 8

| | Physical analysis data | | | | |
|---|---|---|---|---|---|
| Batch # | Tg/° C. Mean | SD | Mositure content/% Mean | D | PSD (D50)/μm |
| 1 | 104 | 1 | 1.15 | 0.51 | 3.04 |
| 4 | 94 | 3 | 1.06 | 0.11 | 3.10 |
| 6 | 99 | 3 | 1.74 | 0.62 | 3.00 |
| 3 | 100 | 2 | 1.31 | 0.45 | 2.94 |
| 7 | 105 | 1 | 1.06 | 0.19 | 3.11 |
| 5 | 101 | 2 | 0.81 | 0.04 | 3.39 |
| 2 | 101 | 1 | 1.23 | 0.17 | 3.30 |

Chemical Stability

The formulations were analysed for degradation using a UV-HPLC assay, operating under the following conditions set forth in Table 9, below.

TABLE 9

| Chromatographic Conditions | |
|---|---|
| Analytical Column Details (column type, particle size, and column dimensions) | Zorbax Bonus RP 3.5 μm 4.6 × 150 mm or validated equivalent |
| Column Temperature | 60° C. |
| Mobile Phase A | 10 mM Ammonium formate in water |
| Mobile Phase B | 100% Acetonitrile |
| Flow Rate | 1.0 mL per minute |
| Gradient Profile | Time (mins) | % A | % B |
| | 0.0 | 90 | 10 |
| | 30 | 65 | 35 |
| | 35 | 20 | 80 |
| | 35.1 | 90 | 10 |
| | 40 | 90 | 10 |
| Detector Wavelength | 220 nm at Attenuation 2000 (for reporting) and 280 nm |
| Injection volume | 20 μl |
| Data collection time/reporting time | 40 mins |
| Run time | 40 mins |
| Autosampler wash solvent | Water |

The HPLC analysis was conducted immediately after manufacture, after two weeks stored at 50° C./ambient humidity, after one month stored at 50° C./ambient humidity and after three months stored at 40° C. in sealed vials in a heat-sealed, desiccated bag, as referred to in Table 7.

Figure 9:
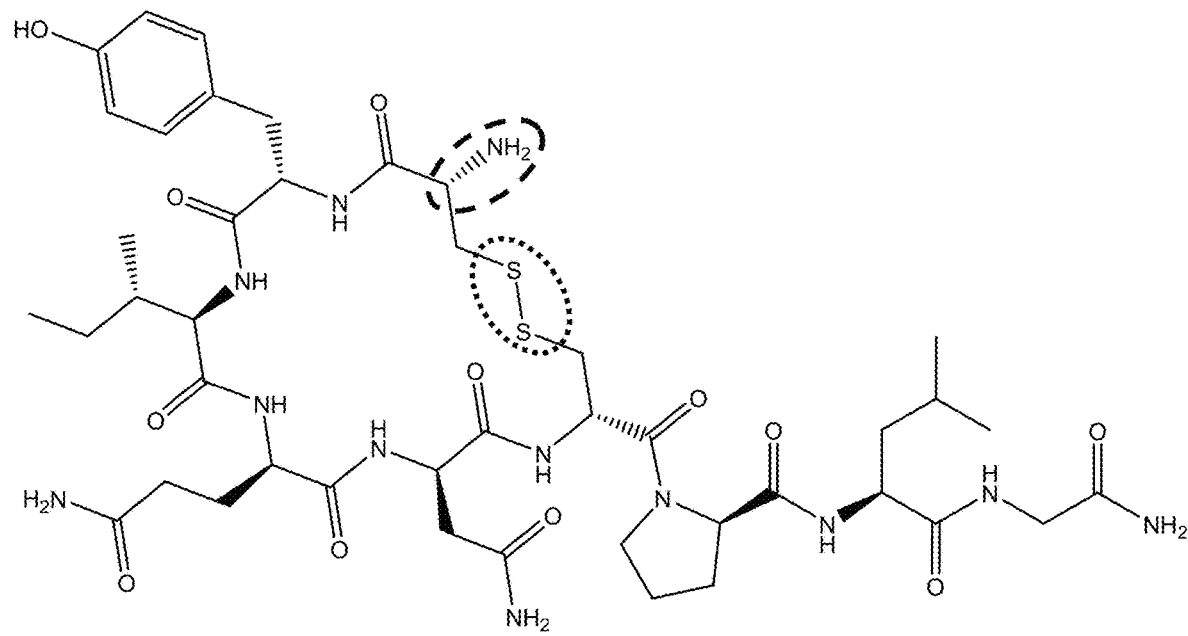
FIG. 9 is a further depiction of the oxytocin molecule with the primary reaction point for the glucose adduct (the NH2) circled in dotted line, and the dimer & trisulphide reaction point (S—S) indicated by the dashed-line circle.
Figure 10:
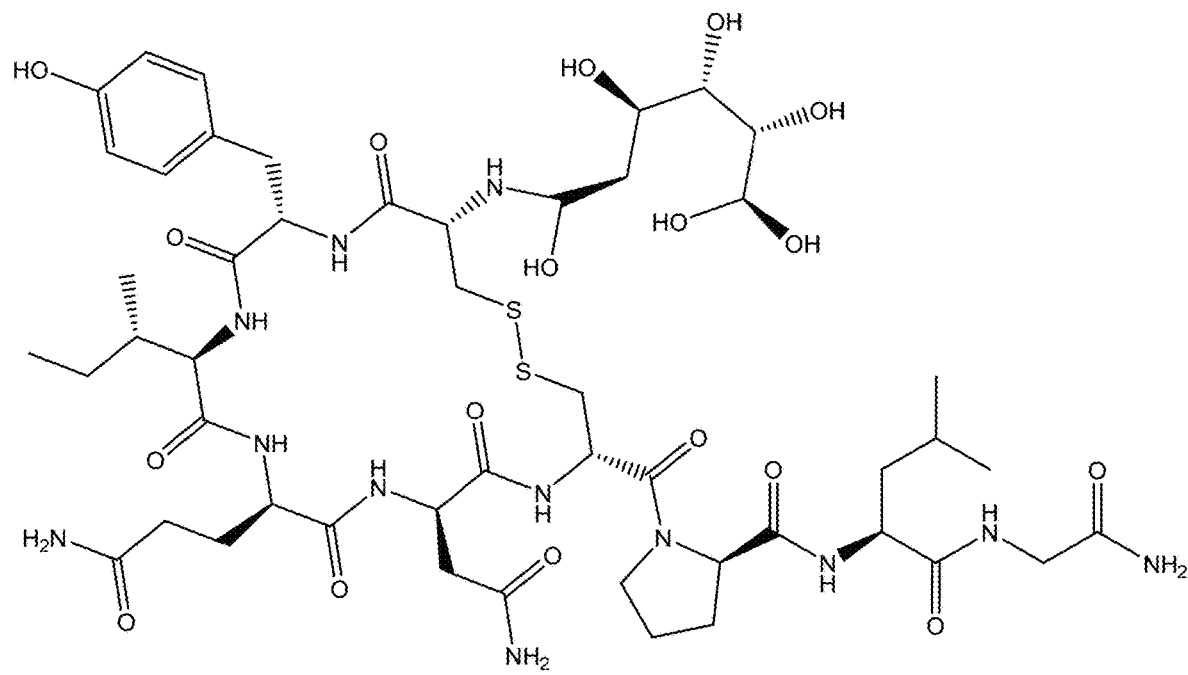
FIG. 10 depicts of the Oxytocin-glucose adduct.
Figure 11:
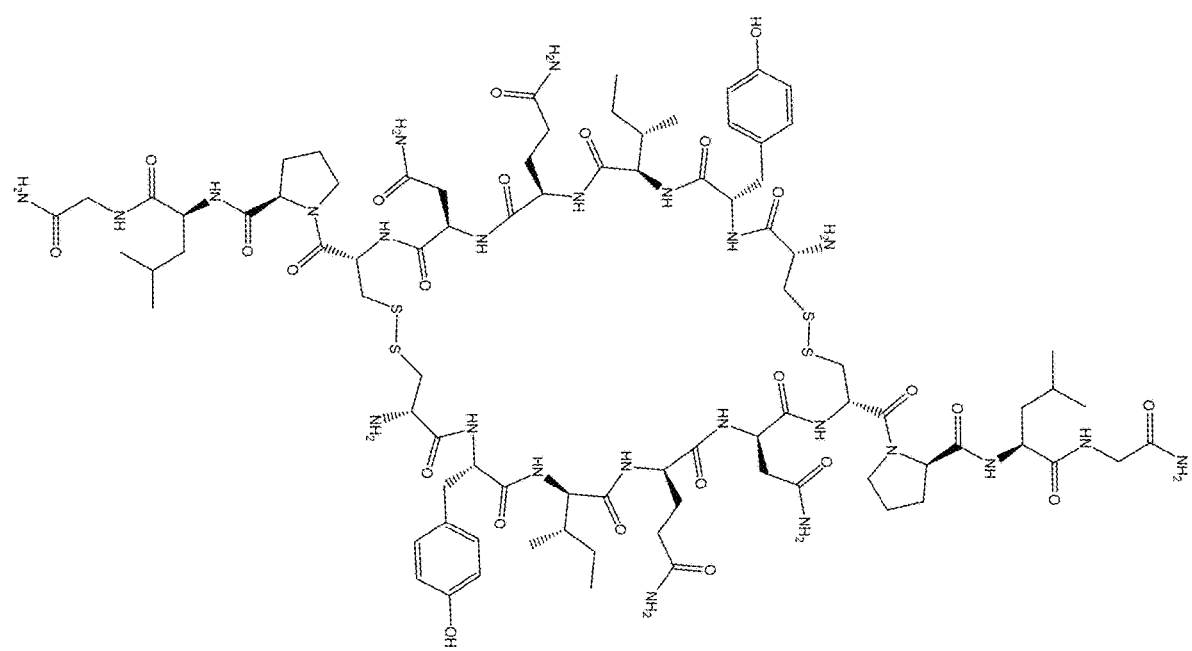
FIG. 11 depicts the α-dimer of oxytocin.
Figure 12:
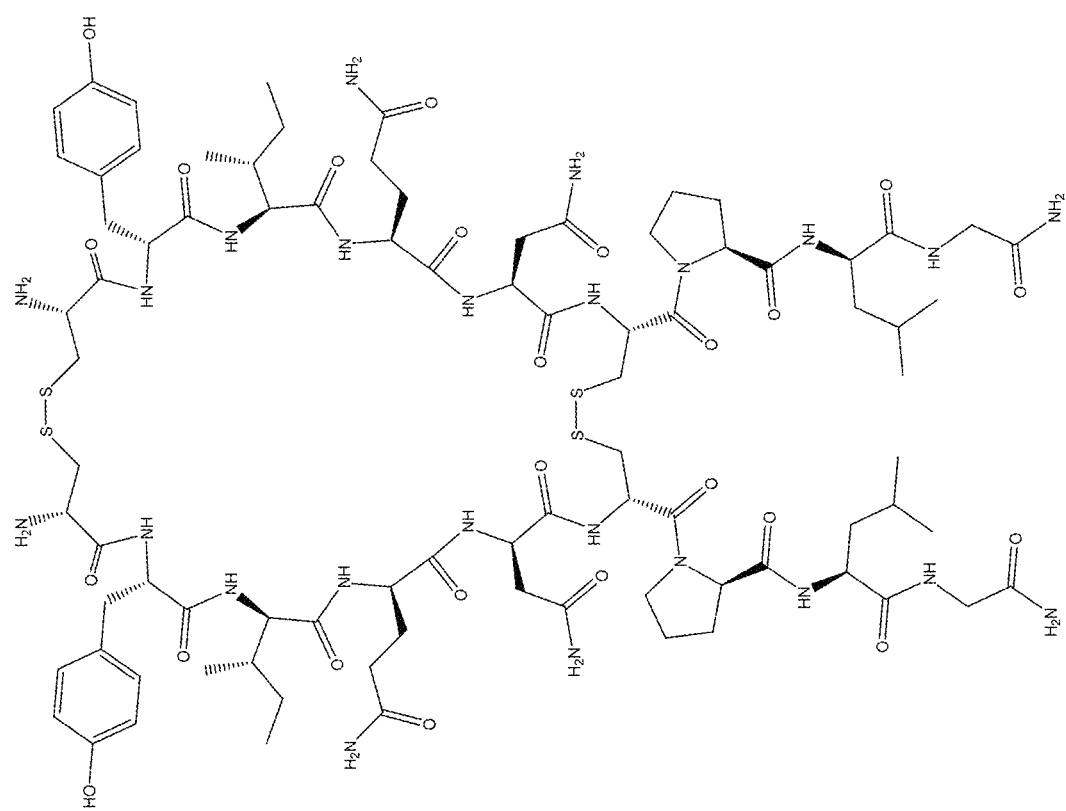
FIG. 12 depiction of the β-dimer of oxytocin.
Figure 13:
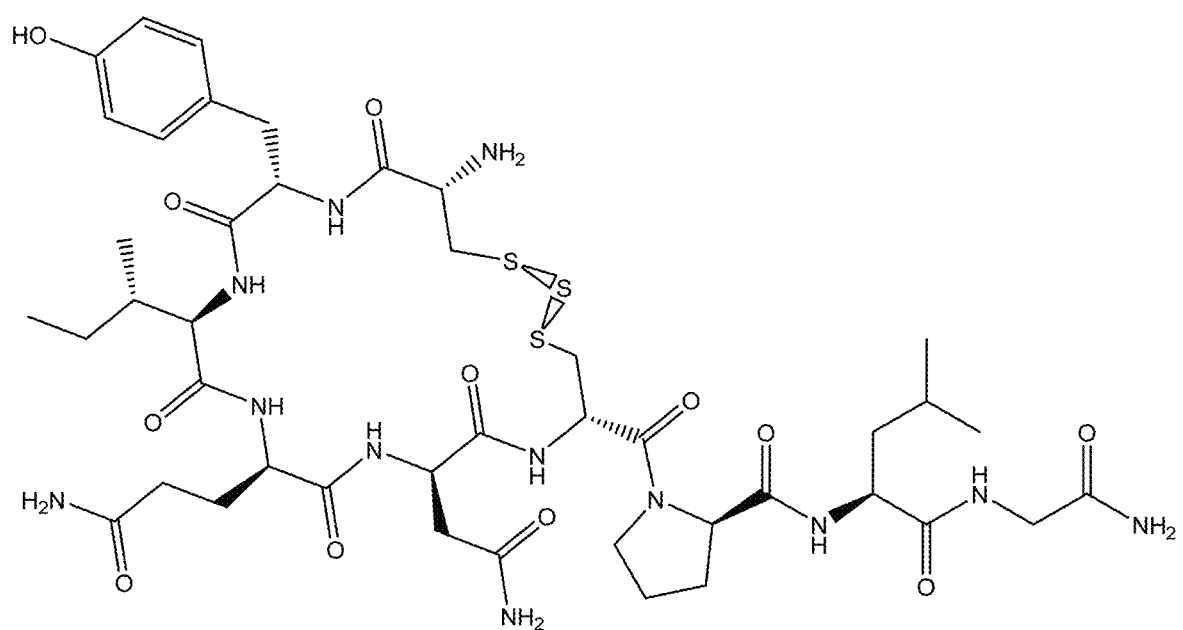
FIG. 13 depicts the tri-sulphide degradant of oxytocin.

The degradants contributing most significantly to the total degradant content are (alpha and beta) dimers, tri-sulphide and glucose related adducts, depictions of which are provided in FIGS. 9-13, below. In these Figures, FIG. 9 depicts the oxytocin molecule, with the primary reaction point for the glucose adduct (the NH2) circled with a dashed-line (the glucose believed to be an impurity in the trehalose used in the experiment), and the dimer & trisulphide reaction point (S—S) circled with a dotted-line. FIG. 10 is a depiction of the oxytocin-glucose adduct. FIG. 11 depicts the α-dimer. FIG. 12 is a depiction of the β-dimer. FIG. 13 depicts the oxytocin tri-sulphide degradant.

Figure 14:
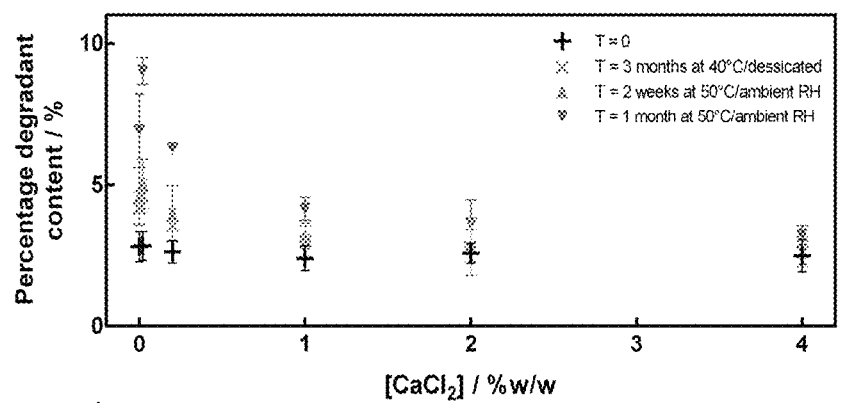
FIG. 14 is a graphical representation of the percentage total degradant content.
Figure 15:
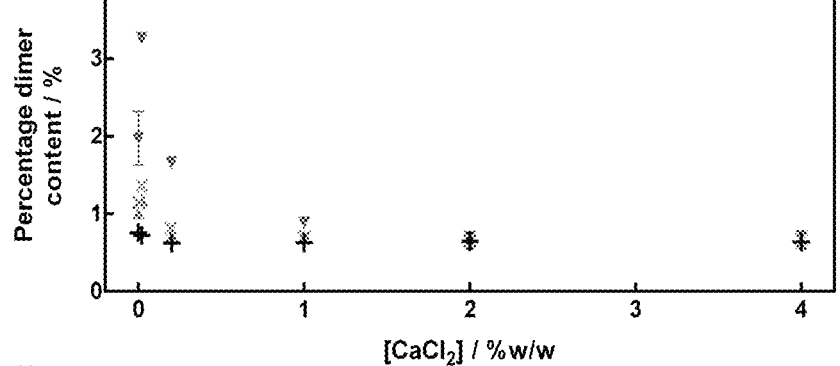
FIG. 15 shows dimer content.
Figure 16:
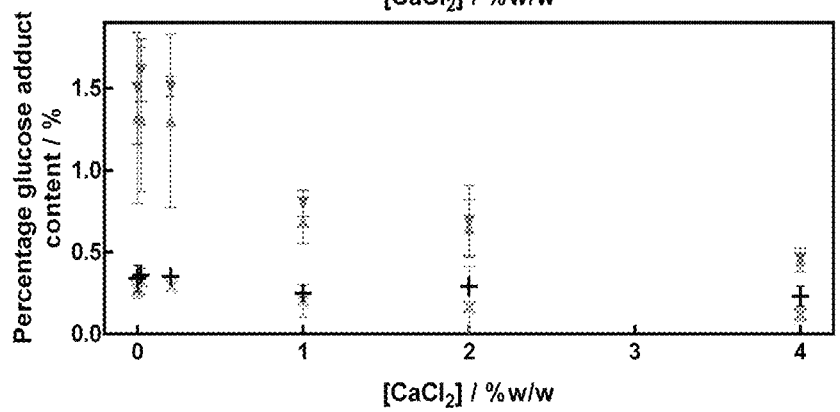
FIG. 16 shows glucose adduct content.
Figure 17:
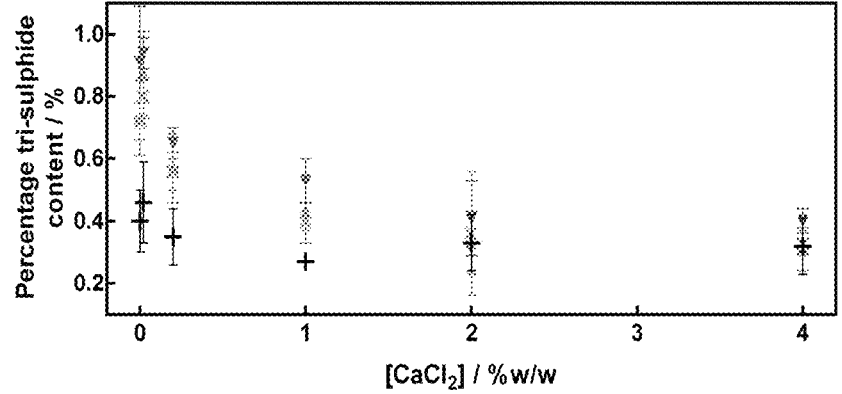
FIG. 17 represents tri-sulphide degradant content.

The results of the stability assay are summarised in the graphs shown in FIGS. 14-17, which represent that data set forth in Table 10, below. FIG. 14 shows the percentage total degradant content. FIG. 15 shows dimer content. FIG. 16 shows glucose adduct content. Lastly, FIG. 17 represents tri-sulphide degradant content.

accelerated stability study, with storage for 1 month at 50° C. and ambient humidity, 1% w/w $CaCl_2$ content or greater was able to reduce dimer formation to no more than zero, which may help set formulation specifications for minimal $CaCl_2$ content. In addition to the reduction in dimer formation, the inclusion of $CaCl_2$ also appears to reduce the formation of the tri-sulphide degradant and the glucose related adduct degradant. While not intending to be bound by any particular scientific theory, these results suggest that the presence of the $Ca^{2+}$ ion interferes with the formation of both of these degradants.

TABLE 10

Chemical stability data

| | Batch # | $CaCl_2$ content/ % | T = 0 Mean | T = 0 SD | T = 3 months at 40° C./dessicated mean | T = 3 months at 40° C./dessicated SD | T = 2 weeks at 50° C./ambient RH Mean | T = 2 weeks at 50° C./ambient RH SD | T = 1 month at 50° C./ambient RH mean | T = 1 month at 50° C./ambient RH SD |
|---|---|---|---|---|---|---|---|---|---|---|
| TOTAL DEGRADANTS | 1/2 | 0.00 | 2.81 | 0.52 | 4.19 | 0.57 | 4.60 | 1.02 | 6.92 | 1.31 |
| | 3 | 0.02 | 2.84 | 0.51 | 4.62 | 0.59 | 5.03 | 0.88 | 9.02 | 0.47 |
| | 4 | 0.20 | 2.63 | 0.39 | 3.59 | 0.55 | 3.98 | 0.99 | 6.28 | 0.21 |
| | 5 | 1.00 | 2.40 | 0.43 | 3.02 | 0.55 | 3.19 | 0.46 | 4.16 | 0.41 |
| | 6 | 2.00 | 2.57 | 0.35 | 2.78 | 1.00 | 2.84 | 0.57 | 3.63 | 0.85 |
| | 7 | 4.00 | 2.49 | 0.58 | 2.63 | 0.52 | 2.61 | 0.41 | 3.22 | 0.34 |
| DIMERS | 1/2 | 0.00 | 0.76 | 0.01 | 1.14 | 0.02 | 1.01 | 0.07 | 1.97 | 0.35 |
| | 3 | 0.02 | 0.72 | 0.05 | 1.35 | 0.00 | 1.18 | 0.06 | 3.26 | 0.07 |
| | 4 | 0.20 | 0.62 | 0.01 | 0.82 | 0.04 | 0.72 | 0.03 | 1.66 | 0.00 |
| | 5 | 1.00 | 0.63 | 0.01 | 0.71 | 0.02 | 0.72 | 0.04 | 0.89 | 0.05 |
| | 6 | 2.00 | 0.65 | 0.02 | 0.65 | 0.08 | 0.62 | 0.01 | 0.70 | 0.05 |
| | 7 | 4.00 | 0.64 | 0.01 | 0.67 | 0.04 | 0.62 | 0.03 | 0.71 | 0.03 |
| TRI-SULPHIDE | 1/2 | 0.00 | 0.40 | 0.10 | 0.72 | 0.06 | 0.73 | 0.12 | 0.91 | 0.18 |
| | 3 | 0.02 | 0.46 | 0.13 | 0.80 | 0.06 | 0.87 | 0.14 | 0.94 | 0.05 |
| | 4 | 0.20 | 0.35 | 0.09 | 0.56 | 0.06 | 0.57 | 0.11 | 0.65 | 0.05 |
| | 5 | 1.00 | 0.27 | 0.01 | 0.40 | 0.03 | 0.43 | 0.10 | 0.53 | 0.07 |
| | 6 | 2.00 | 0.33 | 0.09 | 0.36 | 0.20 | 0.33 | 0.10 | 0.41 | 0.12 |
| | 7 | 4.00 | 0.32 | 0.09 | 0.33 | 0.04 | 0.31 | 0.07 | 0.40 | 0.04 |
| GLUCOSE RELATED ADDUCT | 1/2 | 0.00 | 0.34 | 0.08 | 0.27 | 0.05 | 1.32 | 0.52 | 1.50 | 0.34 |
| | 3 | 0.02 | 0.36 | 0.05 | 0.32 | 0.08 | 1.31 | 0.44 | 1.61 | 0.19 |
| | 4 | 0.20 | 0.35 | 0.04 | 0.29 | 0.01 | 1.30 | 0.53 | 1.51 | 0.06 |
| | 5 | 1.00 | 0.25 | 0.05 | 0.20 | 0.10 | 0.69 | 0.14 | 0.80 | 0.08 |
| | 6 | 2.00 | 0.29 | 0.02 | 0.16 | 0.25 | 0.65 | 0.17 | 0.69 | 0.22 |
| | 7 | 4.00 | 0.23 | 0.06 | 0.12 | 0.04 | 0.45 | 0.07 | 0.46 | 0.02 |

The general trend for total degradant content and the most significant degradants (referring to Table 10 and FIGS. 14-17) is that their formation is reduced when $CaCl_2$ is included in the formulation under all stability conditions and at all time points. This is shown by the highest percentage degradation occurring in formulations with 0% w/w or 0.02% w/w $CaCl_2$ and the lowest degradant formation occurring for formulations containing 2% w/w and 4% w/w $CaCl_2$.

The most significant difference is observed in the samples stored at 50° C. and ambient humidity for 1 month for the total degradant content and the dimer content. However, the tri-sulphide and glucose adduct contents do not appear to increase significantly from storage for 2 weeks at 50° C. to 1 month at 50° C.

A $CaCl_2$ content of 1% w/w or greater appears to significantly reduce the formation of all of these degradants.

These results indicate that the inclusion of divalent cationic material, (e.g. $CaCl_2$) in the formulations studied leads to a reduction in the formation of oxytocin dimers. In an The tri-sulphide degradant reduction could be explained by the same mechanism as the reduction in dimer formation. If the $Ca^{2+}$ ion stabilises the oxytocin ring, the breaking of the di-sulphide bond required to form the tri-sulphide will be impaired. Also, the tri-sulphide may form from the incomplete splitting apart of a dimer, therefore if less dimers are formed, one would expect less tri-sulphide degradant to form.

Finally, the reduction in glucose adduct formation could be explained by the fact that the presence of the $Ca^{2+}$ ion in the vicinity of the oxytocin ring could conformationally impair the amine on the N-terminus cysteine residue of the oxytocin from reacting with glucose to form this degradant.

Although the foregoing invention has been described in some detail by way of illustration and example, for purposes of clarity of understanding, it will be obvious that certain changes and modifications may be practiced within the scope of the appended claims.

What is claimed is:

1. A pharmaceutical composition comprising: composite particles each consisting essentially of:
   (i) oxytocin in an amount of from about 1% to 20%,
   (ii) CaCl$_2$ in an amount of from 0.1% to 5%,
   (iii) L-leucine in an amount of from 10% to 40%, and
   (iv) 10% to 90% trehalose;
   wherein said composite particles have a mass median aerodynamic diameter (MMAD) from about 0.5 μm to about 7.0 μm.

2. The composition of claim 1, wherein the MMAD of the composite particles is about 5 μm or less.

3. The composition of, claim 1 further comprising carrier/diluent particle fraction.

4. The composition of claim 3, wherein the carrier/diluent particle fraction has a MMAD 35 μm or more.

5. The composition of claim 3, wherein the carrier/diluent particle fraction comprises mannitol.

6. The composition of claim 3, wherein the carrier/diluent particle fraction further comprises an additive material to improve the physical or chemical stability or performance of the pharmaceutical composition.

7. The composition of claim 6, wherein the additive material comprises magnesium stearate.

8. A dry powder inhaler comprising the pharmaceutical composition of claim 1.

9. A metered dose inhaler comprising the pharmaceutical composition of claim 1.

10. The inhaler of claim 9, wherein the pharmaceutical composition further includes a pressurized liquid propellant, having said composite particles suspended therein.

11. The inhaler of claim 8, wherein the inhaler provides an emitted dose of least about 20%.

12. A pharmaceutical composition comprising composite particles, each of said composite particles comprising:
   (i) 1% to 10% oxytocin,
   (ii) 0.1% to 5% CaCl$_2$,
   (iii) 10% to 40% L-leucine, and
   (iv) 10% to 90% trehalose;
wherein said composite particles have a MMAD from about 0.5 μm to 5.0 μm.

13. The pharmaceutical composition of claim 12, further comprising pharmaceutically acceptable carrier/diluent particles, wherein the MMAD of said carrier/diluent particles is greater than 10 μm.

14. The composition of claim 13, wherein said pharmaceutically acceptable carrier/diluent particles comprise mannitol.

15. The composition of claim 13, further comprising one or more additive material, wherein the additive material improves the physical or chemical stability or performance of the pharmaceutical formulation.

16. The composition of claim 15, wherein said additive material comprises one or more metal stearates or amino acids, alone or in any combination.

17. The composition of claim 16, wherein the additive material is selected from the group consisting calcium stearate and magnesium stearate, alone or in combination.

18. A method of treating post-partum hemorrhage by the systemic delivery of oxytocin through the lung, comprising the steps of:
   (a) providing an inhaler containing at least one dose of a pharmaceutical formulation according to claim 1,
   (b) dispensing said composite particles from said inhaler,
   (c) delivering at least a portion of said dispersed composite particles to the alveolar region of an individual's lung via inhalation to achieve systemic absorption.

19. The method of claim 18, wherein said composition further comprises pharmaceutically acceptable carrier/diluent particles, wherein the MMAD of said carrier/diluent particles is greater than 10 μm.

20. The method of claim 19, wherein said carrier/diluent particles comprise mannitol.

21. The method of claim 19, further comprising an additive material which improves the physical or chemical stability or performance of the composition.

22. The method of claim 21, wherein the additive material comprises a stearate or amino acid, alone or in any combination.

23. The method of claim 22, wherein the additive material is selected from the group consisting calcium stearate and magnesium stearate, alone or in combination.

24. A unit dosage form for use in a dry powder inhaler comprising a container, said container containing:
   a therapeutic quantity of a pharmaceutical composition of claim 1, and
   a plurality of pharmaceutically acceptable carrier/diluent particles, wherein the MMAD of said carrier/diluent particles is greater than 20 μm.

25. The unit dosage form of claim 24, wherein the carrier/diluent particles comprise mannitol.

26. The unit dosage form of claim 24 further comprising particles of additive material.

27. The unit dosage form of claim 26, wherein the additive material comprises one or more metal stearates or amino acids, alone or in any combination.

28. The unit dosage form of claim 27, wherein the additive material is selected from the group consisting calcium stearate and magnesium stearate, alone or in combination.

29. The unit dosage form of claim 24, wherein the container comprises a capsule.

* * * * *